United States Patent
Pashos et al.

(10) Patent No.: US 10,709,811 B2
(45) Date of Patent: Jul. 14, 2020

(54) SURGICAL GRAFTS FOR REPLACING THE NIPPLE AND AREOLA OR DAMAGED EPIDERMIS

(71) Applicant: THE ADMINISTRATORS OF THE TULANE EDUCATIONAL FUND, New Orleans, LA (US)

(72) Inventors: Nicholas C. Pashos, New Orleans, LA (US); Bruce A. Bunnell, Mandeville, LA (US)

(73) Assignee: The Administrators of the Tulane Educational Fund, New Orleans, LA (US)

(*) Notice: Subject to any disclaimer, the term of this patent is extended or adjusted under 35 U.S.C. 154(b) by 419 days.

(21) Appl. No.: 15/523,306

(22) PCT Filed: Oct. 31, 2015

(86) PCT No.: PCT/US2015/058527
§ 371 (c)(1),
(2) Date: Apr. 28, 2017

(87) PCT Pub. No.: WO2016/070162
PCT Pub. Date: May 6, 2016

(65) Prior Publication Data
US 2018/0015204 A1    Jan. 18, 2018

Related U.S. Application Data

(60) Provisional application No. 62/073,719, filed on Oct. 31, 2014, provisional application No. 62/212,846, filed on Sep. 1, 2015.

(51) Int. Cl.
| | |
|---|---|
| *A61L 27/36* | (2006.01) |
| *A61L 27/38* | (2006.01) |
| *A61F 2/00* | (2006.01) |
| *A61F 2/52* | (2006.01) |
| *A61L 27/22* | (2006.01) |
| *A61L 27/24* | (2006.01) |

(52) U.S. Cl.
CPC ......... *A61L 27/362* (2013.01); *A61F 2/0059* (2013.01); *A61F 2/52* (2013.01); *A61L 27/227* (2013.01); *A61L 27/24* (2013.01); *A61L 27/3604* (2013.01); *A61L 27/3641* (2013.01); *A61L 27/3666* (2013.01); *A61L 27/3687* (2013.01); *A61L 27/3813* (2013.01); *A61F 2002/526* (2013.01); *A61L 2430/04* (2013.01)

(58) Field of Classification Search
CPC .......... A61L 27/362; A61L 2/36; A61L 27/24
USPC ................. 623/11.11, 23.71–23.72
See application file for complete search history.

(56) References Cited

U.S. PATENT DOCUMENTS

| | | | |
|---|---|---|---|
| 8,470,520 B2 | 6/2013 | Ott | |
| 2003/0225355 A1* | 12/2003 | Butler | ........... A61F 2/0063 602/48 |
| 2006/0073592 A1 | 4/2006 | Sun | |
| 2007/0269791 A1* | 11/2007 | Takami | ........... A61L 27/362 435/1.1 |
| 2010/0291058 A1 | 11/2010 | Bowlin | |
| 2013/0028981 A1 | 1/2013 | Gratzer | |
| 2014/0086867 A1* | 3/2014 | Matheny | ........... A61K 35/12 424/85.1 |
| 2014/0276957 A1 | 9/2014 | Locarno | |
| 2016/0106782 A1* | 4/2016 | Frank | ........... A61K 35/28 424/484 |
| 2017/0348088 A1* | 12/2017 | Bunce | ........... A61F 2/105 |
| 2018/0280579 A1* | 10/2018 | Rolle | ........... C07K 14/78 |
| 2018/0338999 A1* | 11/2018 | Brown | ........... A61K 38/1891 |
| 2019/0029572 A1* | 1/2019 | Wisniewski | ........... A61B 5/742 |
| 2019/0255217 A1* | 8/2019 | Early | ........... A61K 9/70 |

FOREIGN PATENT DOCUMENTS

| | | |
|---|---|---|
| WO | 2015134618 A1 | 9/2015 |
| WO | 2015058527 | 1/2016 |

OTHER PUBLICATIONS

Bonvallain, R., et al., "A Nonhuman Primate Model of Lung Regeneration: Detergent-Mediated Decellularization and Initial In Vitro Recellularization with Mesenchymal Stem Cells". Tissue Engineering Part A, online Aug. 22, 2012, pp. 2437-2452, vol. 18, issues 23-24, Mary Ann Liebert, Inc.
Hoganson, D., et al., "Differentiation of human bone marrow mesenchymal stem cells on decellularized extracellular matrix materials," J Biomed Mater Res Part A, online Nov. 13, 2013, pp. 2875-2883, v. 102A, Wiley Periodicals, Inc.
Nimboriboonporn, A., et al., "Nipple-areola complex reconstruction", Gland Surgery, Feb. 2014, pp., 35-42, v. 3 (1). AME Publishing Company.
Scarrit, M., et al., "Hypertensive Rat Lungs Retain Hallmarks of Vascular Disease upon Decellularization but Support the Growth of Mesenchymal Stem Cells," Tissue Engineering: Part A, online: Feb. 2014, pp. 1426-1443, vol. 20, Nos. 9-10. Mary Ann Liebert, Inc.
Su et al., Enhancement of skin wound healing with decellularized scaffolds loaded with hyaluronic acid and epidermal . . . , Matl Sci and Engineering C, 2014, pp. 440-448, v. 44.
Grinnell et al., Reconstitution of human epidermis in vitro is accompanied by transient activation of basal keratinocyte spreading, Exp, Cell Res., 1987, pp. 439-449, v. 172.
Anderson, K.L., Response to Non-Final Office Action dated May 30, 2019,_ dated Dec. 2, 2019, in file of U.S. Appl. No. 15/626,058.
Cerqueira, B.G., Declaration Under 37 C.F.R. i 1.132 of Bianca G. Cerqueira, Ph.D., dated Dec. 2, 2019, Exhibit A to Response in file of U.S. Appl. No. 15/626,058.

* cited by examiner

Primary Examiner — Suzette J Gherbi
(74) Attorney, Agent, or Firm — Laurence J. Hyman; Hyman IP Law

(57) ABSTRACT

The present disclosure relates to surgical grafts for replacing nipples and areolas lost to disease or trauma with surgical grafts of decellularized donor nipples and areolas and to placing and recellularizing such grafts. The disclosure further provides methods for decellularizing epidermis. The decellularized epidermis can be used as a protective cover for skin wounds.

75 Claims, 9 Drawing Sheets

Decellularization Process

FIG. 7
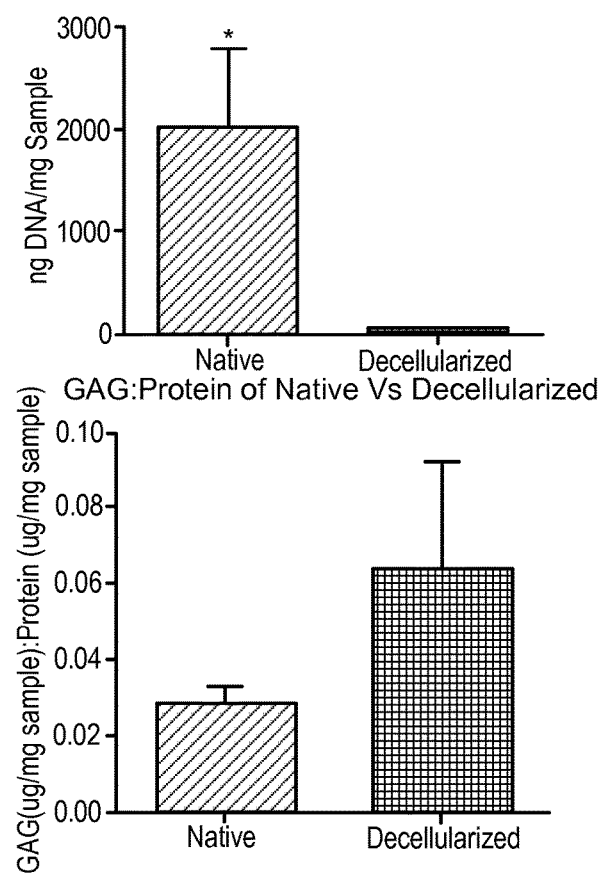
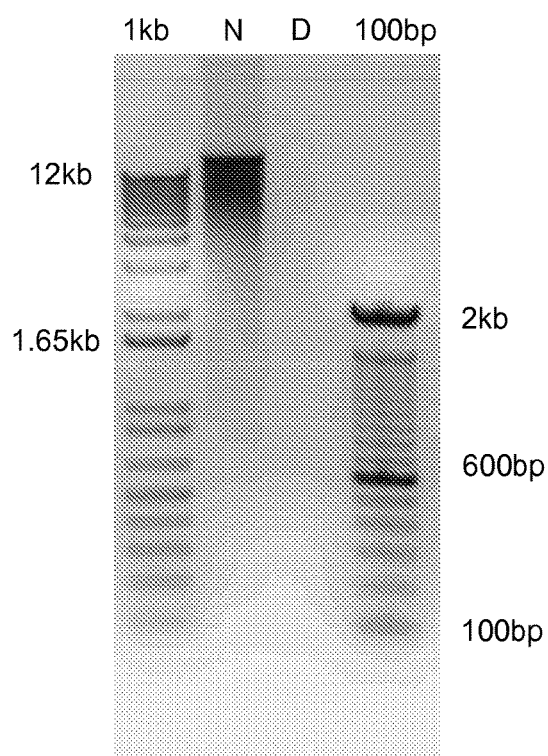

SURGICAL GRAFTS FOR REPLACING THE NIPPLE AND AREOLA OR DAMAGED EPIDERMIS

CROSS-REFERENCE TO RELATED APPLICATIONS

This application is a national stage application under 35 U.S.C. § 371 of International Application No. PCT/US2015/058527 and claims the benefit and priority of U.S. Provisional Patent Application No. 62/073,719, filed Oct. 31, 2014, and of U.S. Provisional Patent Application No. 62/212,846, filed Sep. 1, 2015. The contents of each of these applications are hereby incorporated by reference in their entireties.

STATEMENT OF FEDERAL FUNDING

Not applicable.

PARTIES TO JOINT RESEARCH AGREEMENT

Not applicable.

REFERENCE TO SEQUENCE LISTING OR TABLE SUBMITTED ON COMPACT DISC AND INCORPORATION-BY-REFERENCE OF THE MATERIAL

Not applicable.

BACKGROUND OF THE INVENTION

In the United States alone, over 40,000 women die from breast cancer each year, and more than 230,000 new cases are diagnosed; and there are approximately 430 deaths and 2,000 new cases expected for men. Additionally, there are more than 2.8 million breast cancer survivors in the United States, many of who have undergone reconstructive surgery. Approximately 36% of patients with early-stage diagnoses and 60% of patients with late-stage diagnoses undergo mastectomies. Moreover, immediate breast reconstruction following mastectomies has become more common, from 20.8% in 1998 to 37.8% in 2008. This increasing trend is not surprising as breast reconstruction likely provides psychological benefits for women who undergo mastectomies. There is evidence to suggest that nipple and areola reconstruction affects psychological wellbeing by enhancing body image and self-esteem or decreasing the feeling of distress felt by female patients with mastectomies. Evidence also suggests that women are more comfortable with getting a mastectomy if the nipple can be spared during the mastectomy procedure or if nipple reconstruction is possible, if a nipple-sparing mastectomy is not an option. Currently, there are 180,000 mastectomies performed each year in the United States, with roughly 52,000 women receiving immediate reconstruction following mastectomy. However, immediate breast reconstruction with autologous tissue rarely involves nipple reconstruction and nipple reconstruction typically occurs after the initial reconstruction of the breast.

Surgeons have spent decades developing surgical techniques in the hope of improved solutions to nipple reconstruction. The S flap, for example, was reported in 1988 (Cronin et al., Plast. Reconstr. Surg. 81:783 (1988)). Current strategies for nipple and areola reconstruction are limited to surgical techniques that create a nipple structure from existing local tissue, secondary site grafting, 3D tattooing, or using commercially available acellular dermal matrix sheets, such as AlloDerm® or Glyaderm®. Commonly used surgical techniques to reconstruct a nipple, along with tattooing when desired to add pigmentation, include: nipple reconstruction with areola tattoo, nipple and areola reconstruction with tattoo, nipple reconstruction with skin graft to areola, double opposing tab nipple reconstruction, and C-V Flap nipple reconstruction.

Despite the decades of efforts, satisfactory surgical solutions to maintaining nipple projection following nipple reconstruction has remained a difficult problem. For example, in 2002, Shestak et al. reported using three different techniques, the bell flap, the modified star flap, and the skate flap, to reconstruct nipples on patients and then following the patients to determine whether nipple projection was maintained over time. Patients treated with the bell flap procedure lost so much nipple projection after six months that the authors recommended against using it in virtually any patient. Shestak et al., Plast. Reconstr. Surg. 110(3): 780-6 (2002).

Surgical methods in general have proved less than ideal because nipple and areola reconstruction are highly dependent on surgical technique and existing tissue. Multiple tattooing sessions are required to achieve the optimal coloration, and tattoo can fade to 40% over time. Double opposing tab nipple reconstruction often leads to necrosis of tissue and faulty nipple reconstruction. C-V Flap nipple reconstruction has to be done during the breast reconstruction. To date, no surgical technique has emerged as fully satisfactory. Further, no tissue engineering strategies have been reported that successfully reconstruct the nipple and areola.

There exists a need for a more naturally aesthetic architecture for nipple and areola reconstruction. Surprisingly, the inventive methods and grafts fill this and other needs.

BRIEF SUMMARY OF THE INVENTION

The present invention provides grafts and methods for providing grafts to replace nipples and areolas, and to provide decellularized epidermis.

In a first group of embodiments, the invention provides surgical grafts for grafting to a patient. The graft comprises a decellularized nipple, a decellularized areola, or a decellularized nipple attached to a decellularized areola, which decellularized nipple, areola or nipple attached to an areola substantially retains at least one cell adhesion molecule selected from the group consisting of laminin, elastin, fibronectin, and collagen VI. In some embodiments, the surgical graft is of a decellularized human nipple. In some embodiments, the surgical graft is of a decellularized human areola. In some embodiments, the surgical graft is of a decellularized human nipple attached to a decellularized human areola. In some embodiments, the surgical graft substantially retains laminin, fibronectin, and collagen VI. In some embodiments, the surgical graft has been at least partially repopulated by cells after decellularization. In some embodiments, the cells repopulating the surgical graft are keratinocytes. In some embodiments, the keratinocytes are derived from cells from said patient.

In another group of embodiments, the invention provides methods of making a surgical graft to replace a body part on a patient. The body part has an epidermis and a dermis, and is selected from the group consisting of a nipple, an areola, and a nipple attached to an areola. The method comprises (a) obtaining a donor nipple, an areola, or a nipple attached to an areola, and, (b) decellularizing the nipple, areola, or nipple attached to an areola to decellularize cells of the epidermis and cells of the dermis, while substantially retaining at least one cell adhesion molecule selected from the group consisting of laminin, fibronectin, and collagen VI, thereby providing the surgical graft. In some embodiments, the method further comprises step (c), incubating the decellularized body part with cells exogenous to the body part under conditions conducive to repopulating said body part with the exogenous cells or cells derived from the exogenous cells. In some embodiments, the exogenous cells are keratinocytes derived from the patient. In some embodiments, the decellularization is by contacting said body part with at least a first detergent and performing a first incubation under conditions sufficient to decellularize the epidermis and the dermis in the body part. In some embodiments, the detergent is selected from the group consisting of: 4-(1,1,3,3-Tetramethylbutyl)phenyl-polyethylene glycol, sodium dodecyl sulfate, octylphenoxypolyethoxy-ethanol, 3-[(3-Cholamidopropyl)dimethylammonio]-1-propanesulfonate (CHAPS), and a soluble bile salt. In some embodiments, the conditions sufficient to decellularize the epidermis and the dermis in the body part include incubating the body part with the at least one detergent at room temperature for at least two days. In some embodiments, the method further comprises washing the first detergent from the body part following the first incubation and incubating the body part with a second detergent under conditions sufficient to decellularize the epidermis and the dermis in the body part. In some embodiments, the decellularization is of substantially all epidermal cells and substantially all dermal cells in the body part. In some embodiments, the body part is a nipple attached to an areola.

In a further group of embodiments, the invention provides methods of grafting to a patient in need thereof a body part having an epidermis and a dermis, and selected from the group consisting of a decellularized nipple, a decellularized areola, and a decellularized nipple attached to a decellularized areola, the method comprising: (a) obtaining a donor nipple, an areola, or a nipple attached to an areola, and (b) decellularizing the nipple, areola, or nipple attached to an areola to decellularize substantially all cells of the epidermis and the dermis while substantially retaining at least one cell adhesion molecule selected from the group consisting of laminin, elastin, fibronectin, and collagen VI, (c) optionally, repopulating at least some of the decellularized nipple, areola, or nipple attached to an areola with cells exogenous to the body part, (d) securing the body part to a prepared site on the patient to graft the body part to the patient, and (e) covering the body part with a biocompatible occlusive coating, thereby grafting the body part to the patient. In some embodiments, the method further comprises step (f), allowing time for cells from the patient to integrate into the body part. In some embodiments, the body part is a decellularized nipple attached to a decellularized areola. In some embodiments, the cells exogenous to the body part are keratinocytes. In some embodiments, the keratinocytes are derived from cells from the patient. In some embodiments, the biocompatible occlusive coating is selected from the group consisting of a tissue sealant, a tissue adhesive and a wound sealant. In some embodiments, the biocompatible occlusive coating is 2-octyl cyanoacrylate. In some embodiments, the repopulation in optional step (c) is by incubating the decellularized nipple, areola, or nipple attached to an areola with the exogenous cells ex vivo.

In yet a further group of embodiments, the invention provides compositions comprising a substantially decellularized epidermis substantially retaining at least one cell adhesion molecule selected from the group consisting of laminin, elastin, fibronectin, and collagen VI. In some embodiments, the composition further comprises substantially decellularized dermis substantially retaining at least one cell adhesion molecule selected from the group consisting of laminin, fibronectin, and collagen VI.

In still a further group of embodiments, the invention provides methods of providing a protective cover to a skin surface wound. The methods comprise (a), covering the skin surface wound with a composition comprising substantially decellularized epidermis, which epidermis substantially retains at least one cell adhesion molecule selected from the group consisting of laminin, fibronectin, elastin and collagen VI and, optionally, further comprises substantially decellularized dermis, which dermis substantially retaining at least one cell adhesion molecule selected from the group consisting of laminin, fibronectin, and collagen VI. In some embodiments, the method further comprises step (b), covering the composition on the skin surface wound with a biocompatible occlusive coating. In some embodiments, the substantially decellularized epidermis is at least partially repopulated with cells exogenous to the epidermis prior to step (a). In some embodiments, the cells exogenous to said epidermis are keratinocytes. In some embodiments, the keratinocytes are cells from or derived from cells from the patient. In some embodiments, the biocompatible occlusive coating is selected from the group consisting of a tissue sealant, a tissue adhesive and a wound sealant. In some embodiments, the biocompatible occlusive coating is 2-octyl cyanoacrylate.

In another group of embodiments, the invention provides methods for substantially decellularizing epidermis. The methods comprise contacting the epidermis with at least a first detergent and performing a first incubation under conditions sufficient to substantially decellularize the epidermis. In some embodiments, the detergent is selected from the group consisting of: 4-(1,1,3,3-Tetramethylbutyl)phenyl-polyethylene glycol, sodium dodecyl sulfate, octylphenoxypolyethoxy-ethanol, 3-[(3-Cholamidopropyl)dimethylammonio]-1-propanesulfonate (CHAPS), and a soluble bile salt. In some embodiments, the conditions sufficient to substantially decellularize the epidermis include incubating the epidermis with the at least one detergent at room temperature for at least two days. In some embodiments, the method further comprises washing the first detergent from the epidermis following the first incubation and incubating the epidermis with a second detergent under conditions sufficient to substantially decellularize additional cells of the epidermis.

BRIEF DESCRIPTION OF THE DRAWINGS

FIG. 6 depicts Laminin (A-D; Fibronectin (E-H); Collagen VI (I-L); Secondary Only Control (M-P) and IgG1 Control (Q-T).

FIG. 7 shows a quantification of DNA levels and fragmentation and GAG: Protein ratio A) Average ng DNA/mg of lyophilized tissue of native vs. decellularized matrix, values of 2,022.71 (SEM: 751.90) ng and 56.51 (SEM: 8.45) ng, respectively; with a significant difference of $P<0.05$. B) Agarose gel of Native and Decellularized Nipple Scaffold. C) Glycosaminoglycans to Protein Concentration, with no significant different between native, 0.068 (SEM: 0.027), and decellularized, 0.025 (SEM: 0.004).

DETAILED DESCRIPTION

Introduction and Overview

Figure 1:
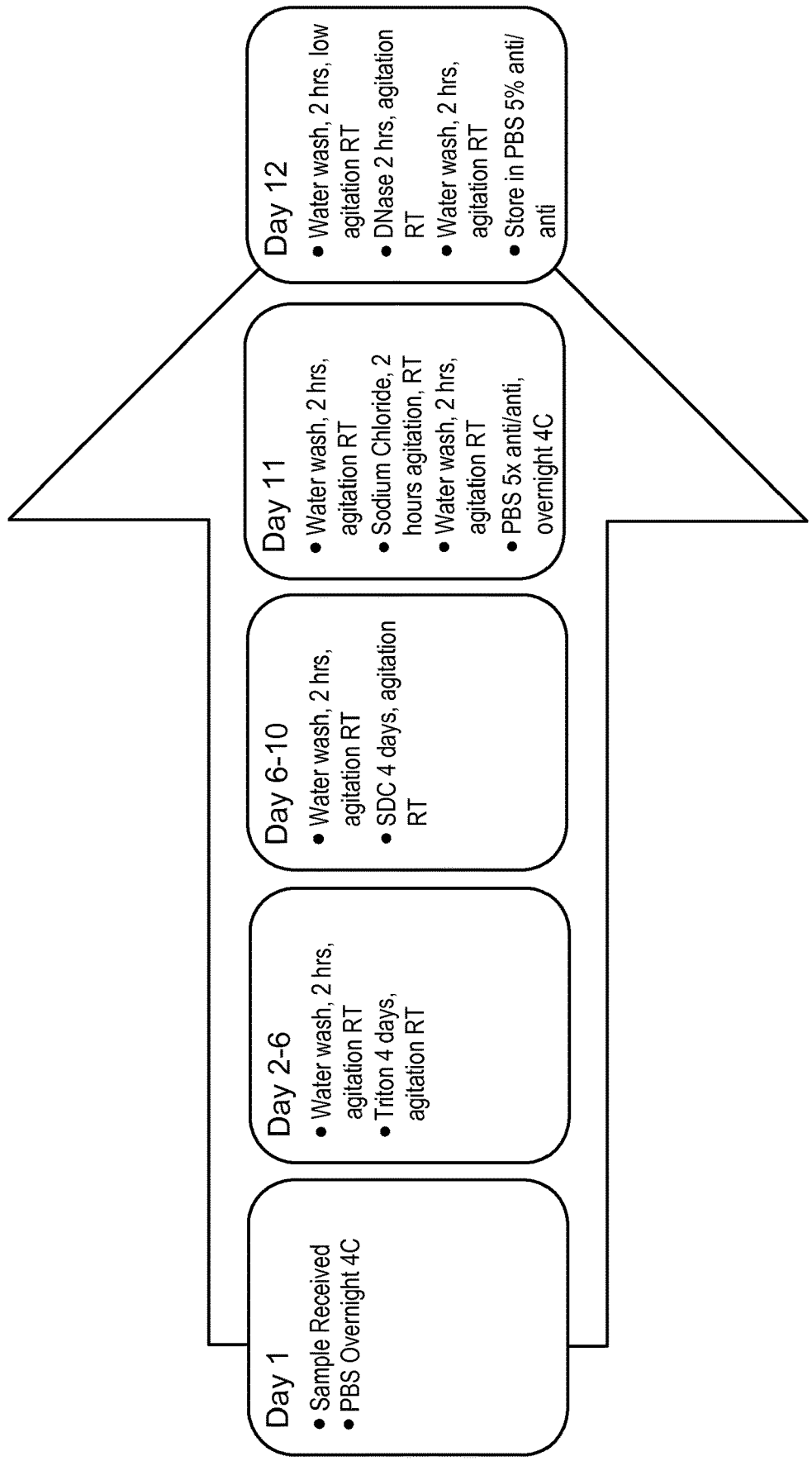
FIG. 1 shows an outline of the decellularization process. Triton=Triton® X-100. "Anti/anti" is an abbreviation for "anti-bacterial/anti-fungal," and refers to a combination of streptomycin, penicillin, and amphotericin B.
Figure 2:
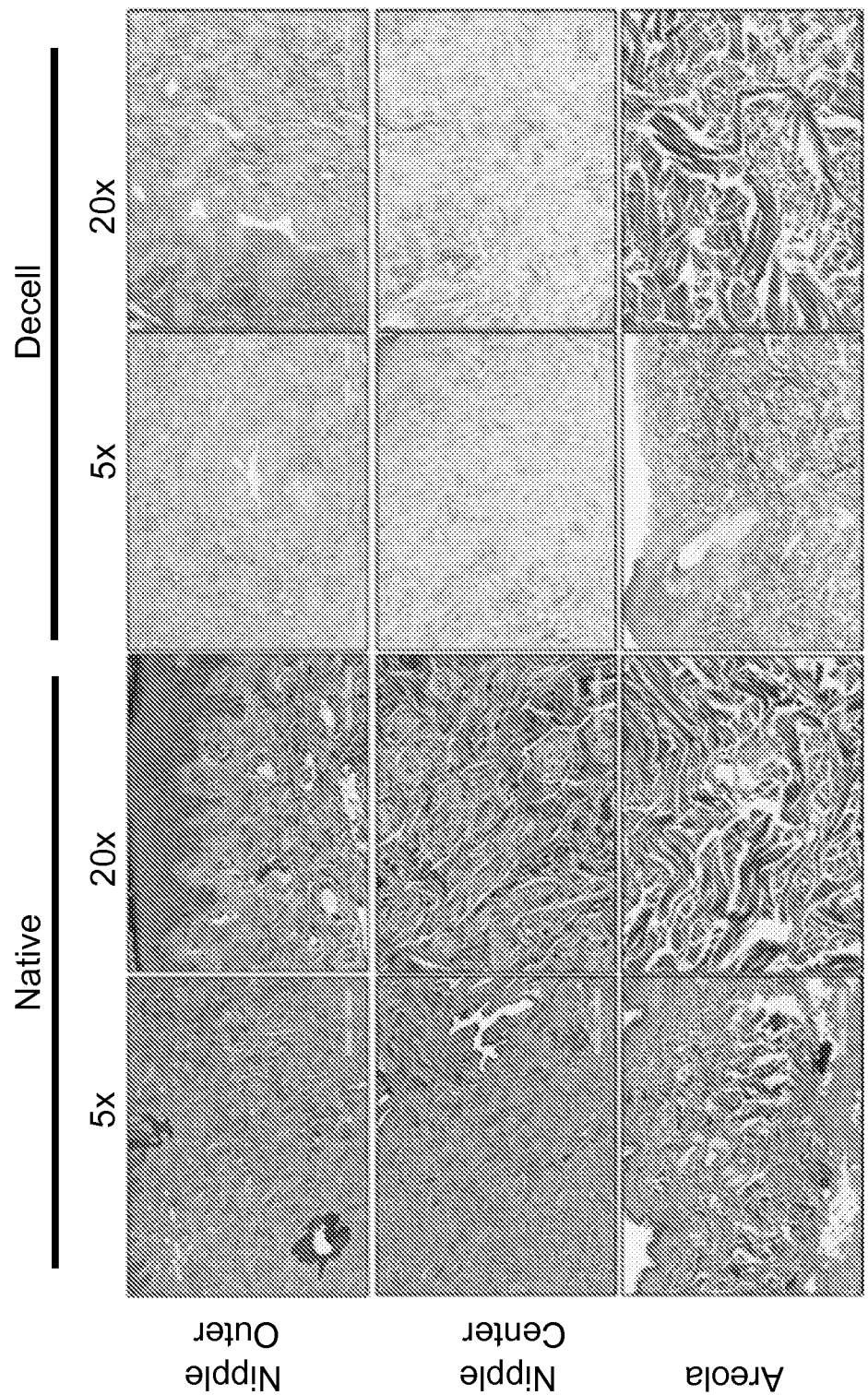
FIG. 2 shows the histological visualization of decellularized extracellular matrix, in comparison with the native tissue.
Figure 3:
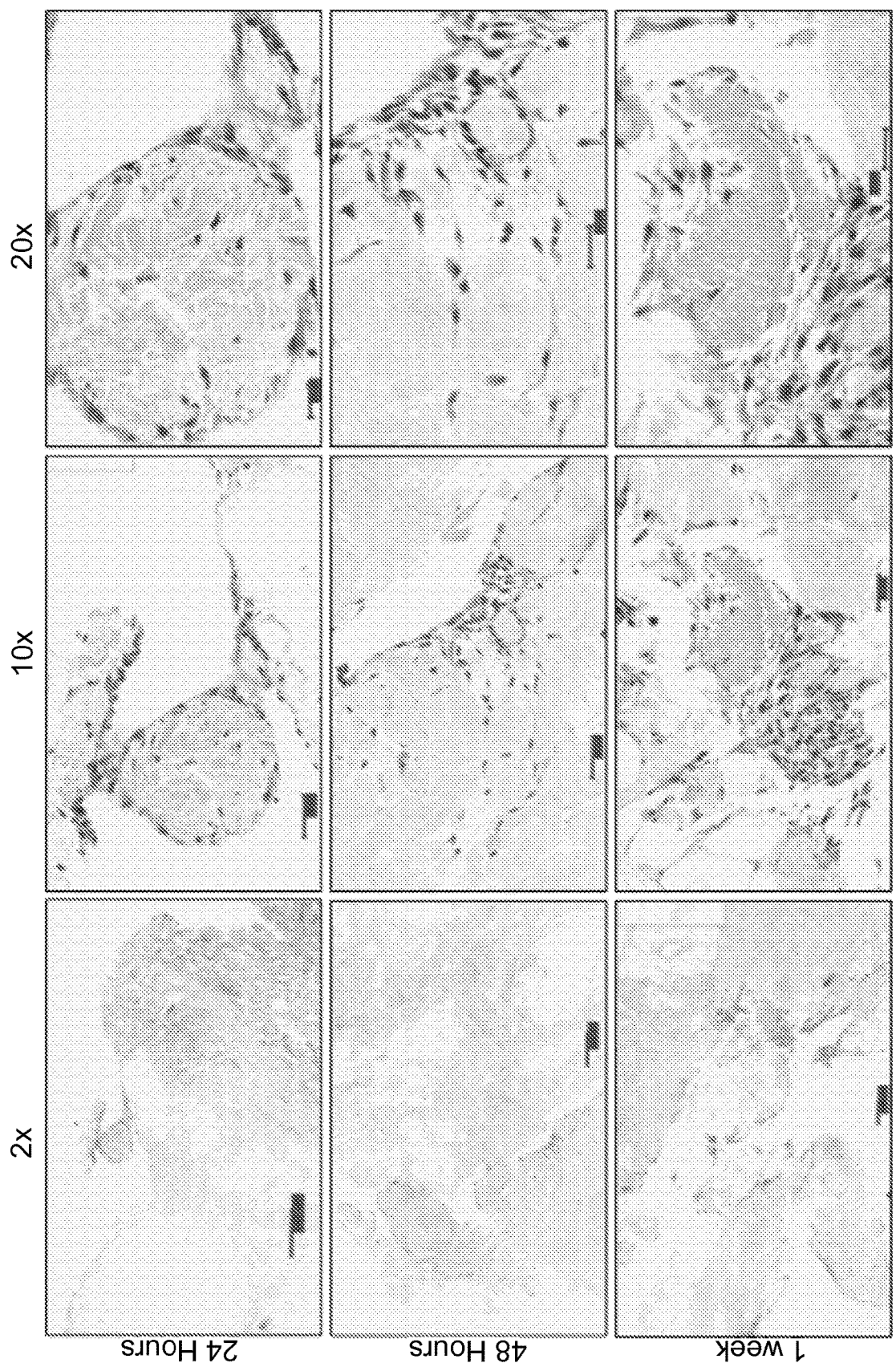
FIG. 3 shows the histological visualization of recellularization of the decellularized scaffold at 24 hours, 48 hours, and 1 week.

As discussed in the Background section, providing an aesthetically satisfying nipple reconstruction is an important part for many patients of breast reconstruction following mastectomy or other surgeries which result in removal of the nipple or nipple and areola. As also noted in the Background, decades of work have resulted in numerous surgical methods to reconstruct the nipple. These surgical procedures, however, rely on constructing the nipple using flaps of tissue either locally disposed on the reconstructed breast or grafted from other sites, such as the thigh or buttock, on the patient's body. While most of all of the procedures provide a nipple mound that can recreate some of the height (projection) and shape of a natural nipple, surgically created flaps lose some of their projection over time.

Surprisingly, the studies reported herein reveal that a nipple and, preferably the accompanying areola, removed from a patient or a cadaver ("donor nipple and donor areola") can be decellularized while retaining their natural gross structures, microarchitecture, and cell adhesion molecules, including collagen, fibronectin, elastin and glycosaminoglycans. This is surprising, in part, because decellularizing the nipple and the areola requires decellularizing epidermis, which proved to be resistant to decellularization by protocols used to decellularize internal organs.

The decellularized structures therefore provide scaffolds into which keratinocytes readily migrate and repopulate. The decellularized structures therefore can be used as grafts that, in the case of a nipple, retain the shape and projection of the donor nipple and, in the case of an areola, that recapitulates the size and shape of the donor areola. The studies underlying the present disclosure used nipples from Rhesus macaque monkeys as a model. Rhesus macaque nipples project further from the breast than do typical human nipples and thus would be expected to be more challenging to decellularize than would human nipples. Given the success in decellularizing macaque nipples, it is expected that the procedures for decellularizing the nipples will work in decellularizing human nipples. Since the grafts and methods are intended to provide cosmetic improvement, they will likely not be used in veterinary applications, but grafts of nipples for other species can be made by the methods disclosed herein if desired.

As persons of skill are aware, in most cases, the nipple and areola are removed together. There is some variation, however, depending on the circumstances of the patient, and in some instances, the areola is removed but not the nipple, while in other instances, the nipple is removed, but not the surrounding areola. The present invention can provide grafts suitable for replacing the nipple alone or for replacing the areola alone. In most surgeries, however, the nipple and areola will be excised from a donor as an attached unit and grafted together onto the recipient as an attached unit. As this is expected to be the most common embodiment, for convenience of reference the discussion below will generally refer to excisions of the nipple and areola for grafting as a unit as a "nipple-areola complex" (as further described and defined below), or "NAC", but will be understood to include embodiments in which only the nipple or only the areola are excised and prepared for use as a graft, or in which the nipple and areola are excised together but only one is prepared for grafting, unless otherwise specified or required by context. As the nipple, areola, or NAC are most commonly intended for grafting to a prepared bed on the surface of a reconstructed breast, it is expected that the nipple and areola will usually only be excised to the thickness of the surrounding skin layer. That is, the nipple, areola, or both, will generally be excised to the depth of the epidermis, dermis or hypodermis of the surrounding tissue.

To obtain a nipple-areola complex for grafting, a nipple-areola complex is first excised from a donor. The donor nipple-areola complex is then decellularized. In a preferred group of embodiments, the decellularization is of both the epidermis as well as the dermis. In studies underlying the present disclosure, we found that protocols we had used to decellularize the lung did not successfully decellularize the epidermis of the NAC. It took a significant amount of experimentation before we found a combination of modifications which together were successful in decellularizing NAC epidermis. The modifications to our decellularization protocols which successfully decellularized the epidermis of the NAC are described below.

Grafting and Coating of Decellularized NAC

In a first group of embodiments, the decellularized NAC can be grafted onto a prepared bed on a patient in need thereof. In these embodiments, it is contemplated that cells from the prepared bed, such as keratinocytes, skin stem cells, melanocytes and fibroblasts, will migrate into the decellularized NAC graft and repopulate it. In these embodiments, the migration of cells into the graft is facilitated by placing the graft on the patient on the prepared bed and then coating the graft and the junction where the graft abuts the patient's skin with a biocompatible substance such as a tissue sealant, tissue adhesive or surgical glue. Without wishing to be bound by theory, it is believed that the "closed wound" environment provided by the use of such substances provides an anoxic environment in which skin cells of various types, especially keratinocytes differentiated from a patient's follicle stem cells or epidermal skin cells, or both, can migrate into and populate the graft. Suitable tissue sealants, adhesives, and surgical glues are described in more detail below. Other biocompatible occlusive coatings that provide an air sealing barrier can be used. It is noted that petroleum jelly would be expected to provide an occlusive coating, but as it may be absorbed and is easily rubbed off against fabric and the like is less durable and would have to be reapplied several times a day to remain effective.

Grafting of Recellularized NAC

In a further group of embodiments, the nipple-areola complex is first decellularized and then repopulated in culture in whole or in part before being grafted onto the patient. In some embodiments, a skin punch is taken from the patient and used as a source of keratinocytes with which to seed the decellularized donor nipple-areola complex. Methods of dissociating cells from a skin sample while retaining cell viability are well known in the art and are set forth in standard sources, such as Freshney, R., Culture of Animal Cells: A Manual of Basic Technique and Specialized Applications (John Wiley and Sons, Inc., Hoboken, N.J., 6$^{th}$ Ed. 2010). Further information about dissociating keratinocytes from primary tissue samples is set forth in more detail in a later section. The choice of the particular dissociation protocol is considered well within the skill of the practitioner. If the patient has a nipple or areola which is healthy, one or more skin punches may be taken from the healthy nipple or areola. This provides a population of melanocytes as well as keratinocytes and may provide a more natural color when used to repopulate the NAC.

Figure 4:
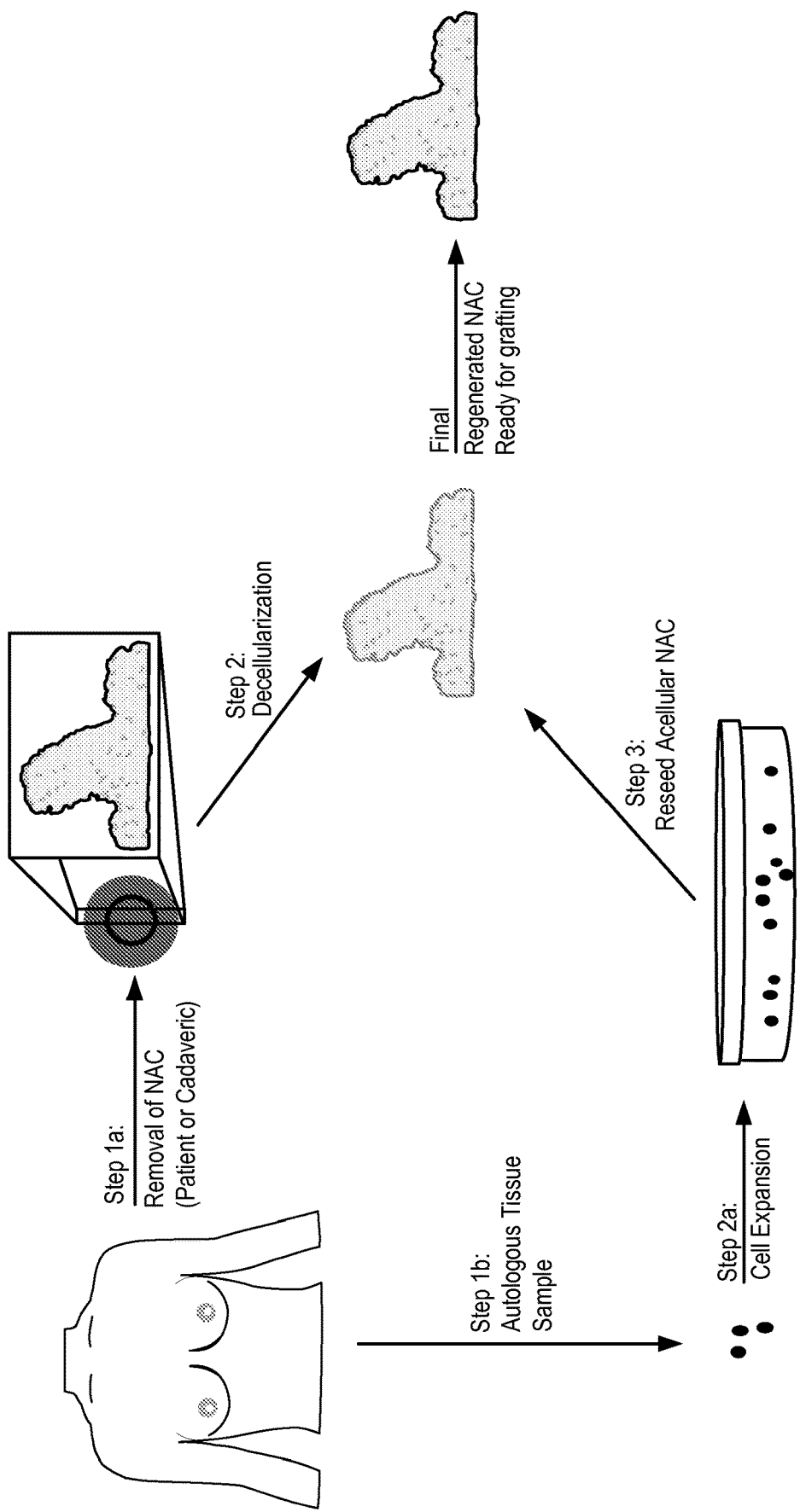
FIG. 4 shows a schematic of the decellularization and recellularization process of the nipple-areolar complex ("NAC"). Step 1a) depicts the removal of the NAC from the patient. Step 2 depicts decellularization of a NAC from the patient; alternatively, this can also represent decellularization of a NAC obtained from a cadaver. In step 1b, an autologous tissue sample, typically from a skin punch, is taken from the patient. In step 2a, cells from the autologous tissue sample are expanded in tissue culture. In step 3, cells from the tissue culture are used to seed the decellularized NAC. After time to allow the autologous cells to repopulate the NAC, the repopulated NAC is ready for grafting ("final step").

Once dissociated, the cells can be placed in contact with the decellularized NAC. Alternatively, the dissociated cells are first expanded in culture, as represented schematically in FIG. 4, step 2a, and then placed in contact with the decellularized NAC. Typically, this is done by placing the decellularized NAC into culture medium containing the dissociated or dissociated and expanded cells and allowing the cells to migrate into the NAC and repopulate it. In some embodiments, however, cells may be injected into one or more places in the NAC, particularly into the interior, to speed repopulation. It is anticipated that repopulation of the NAC may take 5-8 weeks for sufficient, if not complete, repopulation. This period of time is not expected to pose a problem for mastectomy patients as current protocols usually include at least a three month period for the reconstructed breast to heal before nipple reconstruction is performed. Visual inspection of the NAC is preferably performed to verify that the exterior of the NAC is fully repopulated. NACs whose exterior has not been fully repopulated can also be grafted, in which case the graft is preferably coated with a biocompatible occlusive coating, as described above for decellularized NACs.

Typically, the cells that repopulate the NAC are keratinocytes, although other skin cell types may also migrate in. As persons of skill will appreciate, since the repopulated NAC are intended only to provide an aesthetically satisfying recreation of a NAC, it is not necessary to repopulate the decellularized NAC with all the cell types that might be present in a native NAC.

In some embodiments, cells from other appropriate sources or other types of cells are used to seed the decellularized NAC. In some embodiments, the cells used to seed the NAC are melanocytes or epithelial cells. In some embodiments, the cells are adipose-derived stem cells. In some embodiments, the cells are bone marrow-derived stem cells. Sources of each of these kinds of cells are known in the art. It is contemplated that the cell adhesion molecules present in the decellularized NAC will guide the differentiation of the progeny from the skin or other stem cells into cells appropriate for the NAC. Based on the vascularization that has been seen with respect to acellular dermal grafts, it is expected that NAC grafts will likewise become vascularized.

In some embodiments, it is not necessary for the NAC to be fully repopulated by cells before grafting, as it is expected that keratinocytes will migrate into the graft from surrounding skin and continue to populate it after it is grafted into place. In these embodiments, after the NAC is grafted onto the patient, it is preferably covered with a biocompatible occlusive coating, such as a tissue sealant, tissue adhesive or surgical glue, to provide a closed wound environment, as described above for grafting of an acellular NAC.

DEFINITIONS

Units, prefixes, and symbols are denoted in their Systeme International de Unites (SI) accepted form. Numeric ranges are inclusive of the numbers defining the range.

As used herein, "areola" refers to the small circular area around the nipple, not to any other areolas that may be present on a particular individual.

As used herein, "attached" as it relates to a nipple "attached" to an areola means a nipple that has been excised from a donor as a unit with the areola that surrounded it.

As used herein, "autologous" refers to a biological material that will be introduced into the same individual from whom the material was derived.

As used herein, "biocompatible" refers to a material which is not toxic, injurious or inhibitory to mammalian cells, tissues, or organs with which it comes in contact and which in use related to a graft does not provoke an immunological or inflammatory response sufficient to be deleterious to the patient's health or to engraftment of the graft.

As used herein, "decellularized" of a biological tissue or structure refers to removing most or all of the cells of the tissue or structure while substantially preserving the extracellular matrix and associated cell adhesion molecules.

As used herein, "decellularizing substantially all" cells of a described tissue or structure, such as of a nipple or of the epidermis, means that at least 85%, 90%, 95%, 96%, 97%, 98%, 99% or more of the cells present in the tissue or structure have been removed, with each succeeding higher percentage being preferred to the lower percentages. The percentage reduction in the number of cells can be determined by, for example, counting by visual inspection the number of cells visible in samples pre- and post-decellularization, along with DAPI staining to visualize nuclei.

As persons of skill will understand, a tissue can be decellularized and then repopulated or recellularized. A recellularized tissue or structure is not expected to have the combination of cell types that may have been present in the structure before it underwent decellularization.

As used herein, "extracellular matrix" refers to the complex network of macromolecules filling the extracellular space in a tissue and, in particular, a nipple, areola or the skin. The extracellular matrix is composed of glycosaminoglycans (GAGs), often covalently linked to protein forming the proteoglycans, and fibrous proteins, including collagen, elastin, fibronectin, and laminin. As the skin is subject to frequent stretching and bending, it has a relatively high content of elastin and elastic fibers.

As used herein, "extracellular matrix fibrous protein" and "cell adhesion molecule" refer to a fibrous protein of the extracellular matrix, such as fibronectin, laminin, elastin or collagen VI.

As used herein, "exogenous" in relation to cells introduced to recellularize a decellularized tissue means cells that did not originate in the decellularized tissue. By way of example, if a nipple from a patient is decellularized and repopulated with keratinocytes originating from a skin punch taken from the same patient, as used herein, the keratinocytes are still exogenous to the decellularized nipple because they did not originate from the nipple.

As used herein, a "graft" refers to a structure or composition that is implanted or attached to an individual to replace an anatomical feature or to correct an anatomical defect. The grafts described herein typically replace nipples or areolas, or both, that have been surgically removed or have been lost due to trauma.

As used herein, "substantially retaining at least one cell adhesion molecule" with reference to a decellularized structure, such as a decellularized nipple or a decellularized skin layer, such as the epidermis, means that, under immunohistochemical examination of the extracellular matrix of the structure or skin layer, the presence of the cell adhesion molecule can be seen throughout the matrix and that, for proteins that can be quantified, samples of the matrix show that the sample retains 40%, 50%, 60%, 70%, 80%, 90% or more of the amount of the cell adhesion molecule present in the extracellular matrix prior to decellularization, with higher percentages being more preferred than lower ones.

Nipple-Areolar Complex

In medical usage, the phrases "nipple-areolar complex" and "nipple-areola complex" (used interchangeably herein) generally refer to a structure that develops in the breast during gestation, and includes vessels, glands and fibers arranged in a generally radial manner around the nipple, including the Montgomery glands and Morgagni tubercles, smooth muscle cells and a lymphatic system called the subareolar plexus. See, for example, Jones and Pacifici, "Nipple-areola complex," accessed on the website Radiopaedia[dot]org, October 2015; An et al., J Ultrasound Med, 29:949-962 (2010). However, discussions of reconstructing the nipple and areola in women who have lost one or both of theirs to surgery, trauma, or of creating a nipple and areola in the case of congenital absence, often refer to nipple-areola reconstruction interchangeably as reconstruction of the nipple-areola complex, even though what is being reconstructed is just the exterior shape and appearance of the nipple and areola. See, e.g., Chun, Y. S., Nipple-Areola Reconstruction, emedicine.medscape[dot]com/article/1274411-overview, accessed October 2015.

Like traditional surgical flaps recreating the appearance of a nipple and tattooing to create the appearance of an areola, the inventive grafts and methods using them are intended only to provide an aesthetically satisfying appearance of a nipple and areola, not to create a nipple that is functional in producing milk. It is therefore not necessary for the inventive grafts and methods that a decellularized nipple or nipple and areola be recellularized with the different cell types present in a natural nipple-areolar complex. To serve their purpose, only the portion of the nipple projecting above the skin is needed, and only the visible portion of the areola. As used herein, therefore, the phrase "nipple-areola complex" and the abbreviation "NAC" refer to a nipple and areola excised as a unit from a patient or cadaver and do not relate to or include the various structures, vessels or glands underlying under the superficial structures of the nipple or areola.

In some preferred embodiments, the nipple is removed from the donor patient or cadaver along with some or all of the skin layers of the areola. In some embodiments, the skin layers excised are the epidermis and the dermis. In some embodiments, the skin layers excised are the epidermis, the dermis, and the hypodermis, or subcutaneous layer.

Preparation of the Graft Site and Placing of Graft

Surgeons are familiar with placing reconstructed nipples, NACs and tattoos of areolas on breasts that have been reconstructed, and the same techniques can be used to position the inventive grafts. A nipple or NAC reconstruction following mastectomy typically occurs as an outpatient procedure some 3 to 4 months following reconstruction of the breast and is the final phase in the process.

As noted in the Background, surgeons have been performing tissue grafts intended to create the appearance of nipples and areolas for decades and do not need guidance in how to select and prepare a site to receive the inventive grafts. In brief, the site selected to receive the graft is prepared by removing the epidermis, the dermis and, if desired, the subcutaneous layer of the site to provide a bed on which the graft will be positioned. The size and shape of the area from which the skin layers are removed preferably closely matches the size and shape of the nipple, areola or NAC being grafted onto the patient. Once the graft is in position, the graft is typically secured with sutures.

Covering Decellularized Grafts with Biocompatible Occlusive Coating

In embodiments in which the grafts are of decellularized nipple, areola, or NAC that will be recellularized in situ at the graft site, recellularization is facilitated by coating the surface of the graft, as well as the perimeter where the patient's skin abuts the graft, with a biocompatible, occlusive coating. In some preferred embodiments, the occlusive coating is a tissue sealant, tissue adhesive or tissue glue. Without wishing to be bound by theory, it is believed that the use of a tissue sealant not only creates a "closed wound"

with an anoxic environment that promotes migration of keratinocytes into the decellularized matrix of the graft, but also creates a barrier to the infiltration of foreign particles, including bacteria, into the graft. Cyanoacrylates, marine adhesive proteins, fibrin-based sealants, and mixtures of polypeptides and proteoglycans are among the compositions that have been developed as wound sealants. Fibrin glues have been approved for use in the United States since 1998. A fibrin sealant, TISSEEL®, is commercially available, as are BIOGLUE® and DuraSeal®. In some preferred embodiments, the tissue sealant is high viscosity 2-octyl cyanoacrylate, sold commercially under the names DERMABOND® (Ethicon unit of Johnson & Johnson) and Sure+Close®II. It is anticipated that keratinocytes will migrate from the surrounding skin into the decellularized or partially recellularized graft and assist in its engraftment and repopulation.

Culturing Keratinocytes

As noted in a preceding section, in some embodiments, rather than grafting a decellularized nipple, areola or NAC onto the patient and allowing keratinocytes to migrate from the surrounding skin into the graft, the graft is recellularized ex vivo and grafted onto the patient after the desired degree of recellularization has occurred.

In some embodiments, a skin punch taken from the patient is used as a source of cells with which to recellularize the graft. Keratinocytes play a significant role in healing wounds in the skin by migrating to fill the gap in the wound. It is anticipated that keratinocytes will play a large role in repopulating a decellularized nipple, areola, or NAC. A number of techniques are known in the art by which keratinocytes can be isolated from skin for expansion, and those techniques can be used to dissociate the skin punch to activate keratinocyte migration into the graft to repopulate a decellularized nipple, areola, or NAC. For example, Hybbinette et al., Exp Dermatol 8(1):30-8 (1999), compared four techniques for dissociating skin biopsies to identify methods for expansion of isolated keratinocytes. The authors concluded that trypsin:EDTA incubation in a trypsinizing flask or after epidermal-dermal separation using thermolysin, were preferable methods for isolating keratinocytes from human skin. Further, Worthington Biochemical Corporation (Lakewood, N.J.), publishes a "Tissue Dissociation Guide" to provide a compendium of enzymes and conditions for dissociation of a number of tissues, including skin. Protocols for dissociating cells from primary tissue are also set forth on the websites of reagent distributors. For example, the Thermo Fisher Scientific website sets forth four such protocols, including the following protocol using dispase: "(1) Mince tissue into 3 to 4 mm pieces with a sterile scalpel or scissors, (2) wash the tissue pieces several times in a calcium and magnesium-free balanced salt solution, (3) add dispase (0.6 to 2.4 U/ml in calcium and magnesium-free balanced salt solution), (4) incubate at 37° C. for 20 min to several hours. Filter the cell suspension through a sterile, stainless steel or nylon mesh to separate the dispersed cells and tissue fragments from the larger pieces. Fresh dispase can be added to the fragments if further disaggregation is required. Wash suspension several times by centrifugation in the balanced salt solution."

It is expected that persons of skill are familiar with this literature and can readily obtain keratinocytes from one or more skin punches. The keratinocytes can simply be placed in the culture medium, from which they can percolate into the graft. Preferably, they are injected into the graft at one or more locations. The grafts are maintained in a cell culture medium suitable for maintenance and expansion of human primary keratinocytes. To reduce the chance of transmitting disease agents to the patient, the culture medium is preferably serum-free and does not require the use of feeder cells. Suitable media specific for keratinocytes are known in the art and include Keratinocyte Growth Medium 2 (PromoCell GmbH, Heidelberg, Germany) and Stemline™ keratinocyte basal medium (Sigma-Aldrich Corp., St. Louis, Mo.,) and defined, BPE-free medium supplement (K 3136) (Sigma-Aldrich Corp.), and ATCC's Dermal Cell Basal Medium (PCS-200-030) supplemented with Keratinocyte Growth Kit (PCS-200-040).

Tattooing

Whether a graft is recellularized in situ or ex vivo, the cells repopulating the graft will generally be keratinocytes, but not the melanocytes that typically make an areola and nipple darker than the surrounding skin. The graft will generally be tattooed at a later point to the desired color.

Decellularization of Epidermis

In some embodiments, the epidermis of the donor nipple, areola, or NAC, is decellularized along with the dermis. AlloDerm® and Glyaderm®, two commercially available acellular dermal matrices, are used as tissue extenders or dermal replacement for wounds and burns. Neither contains acellular epidermis. It is believed that these materials are made by separating the epidermis from the dermis prior to decellularizing the dermis. Without wishing to be bound by theory, it is believed that this is in part because the epidermis is denser than the dermis and much harder to decellularize.

Others have reported decellularization of organs, as exemplified by U.S. Pat. No. 8,470,520. The organs whose decellularization is reported in this patent include lung, but not skin. We found that a protocol we had previously used successfully to decellularize lung did not work to decellularized nipple epidermis in studies using Rhesus macaque nipples. Specifically, the protocol that had successfully decellularized the lung succeeded in decellularizing approximately 95% of the dermis cells, but only 5% of the epidermal cells. To solve this problem, we performed studies to find protocols that would succeed in decellularizing nipple epidermis. After consideration experimentation, we succeeded in developing modifications that successfully decellularized nipple epidermis, along with the accompanying dermis. Given our results with decellularizing nipple epidermis and dermis, we expect the protocols to work equally well in decellularizing skin epidermis and dermis.

Our protocols for decellularizing the lung comprised the following steps. We first contacted the lung with a dilute solution of a detergent or surfactant capable of permeating eukaryotic cell membranes and solubilizing membrane proteins and incubated it at 4° C. The detergent or surfactant was changed each day. After 4 days, the samples were washed with water for several hours and then contacted and incubated with a 2% solution of a bile salt, sodium deoxycholate ("SDC"), for 4 days at 4° C., with the bile salt solution changed each day. The samples were then subjected to a second wash with water, incubated with DNase I for 2 hours, again at 4° C., washed again with water and then stored. The solutions were introduced into the lung by perfusion.

To decellularize nipples, including the epidermis, we modified the protocol in multiple ways. First, the temperatures of the incubations and washes were raised—rather than conducting them at 4° C., they were conducted at room temperature. Second, rather than changing the solutions each day during the multiple-day incubations, the samples were left in the same solution throughout the incubation. Without wishing to be bound by theory, it was thought this would augment digestion of the cells by not removing any endogenous proteases present in the cells. Third, the times of the incubations were doubled. Fourth, the concentration of the bile salt was doubled, with the concentration of the bile salt raised from 2% to 4%. Fourth, for the lung, the organ was perfused. As nipples do not have vessels allowing ready perfusion, the samples were initially agitated on an orbital shaker set to a rotation speed of 85-125 rpm, which we thought would subject the nipple to solutions in a manner simulating perfusion. We found, however, that the nipple did not decellularize at low speed agitation, but did when the shaker speed was increased to 325 rpm. While none of these changes by themselves or any two or three together were sufficient to decellularize the nipple samples, the combination of all four succeeded.

As the original decellularization protocol worked on the lung, which has airways permitting essentially all the tissue of the organ to be contacted with the detergents and other reagents, but did not work when used on the nipple, the nipple appears to be particularly resistant to decellularization of the epidermis. We believe that the protocol developed for decellularizing the nipple can therefore be used to decellularize other body parts for which an acellular matrix might be useful.

Based on the studies undertaken on the nipple, a sample to be decellularized is contacted with a first detergent or surfactant solution for 48 hours to about 144 hours, more preferably about 72 to about 120 hours, still more preferably about 80 to about 110 hours, even more preferably for about 96 hours, where "about" means±2 hours, which detergent or surfactant can permeate eukaryotic cell membranes and solubilize membrane proteins. Suitable detergents include 4-(1,1,3,3-Tetramethylbutyl)phenyl-polyethylene glycol (Triton™ X-100), octylphenoxypolyethoxy-ethanol (IG-EPAL® CA-630), CHAPS (3-[(3-Cholamidopropyl)dimethylammonio]-1-propanesulfonate), sodium dodecyl sulfate and polyethylene glycol, with the first three being more preferred. The sample is then washed with water, preferably for several hours, and then contacted with an appropriate soluble bile salt as a second detergent for a time period similar to those described above for use with the first detergent, above. Sigma-Aldrich Corp. (St. Louis, Mo.), for example, sells at least the following sodium salts of bile acids: sodium cholate, sodium deoxycholate, sodium glycocholate, sodium taurocholate, and sodium taurodeoxycholate. While all of these salts have sodium as the cation, other cations can be used to form a salt of a bile acid for use in the inventive methods so long as the resulting bile salt is soluble and decellularizes epidermis. Any particular bile salt can be readily tested to see whether it is suitable for its use in decellularizing epidermis by using it in place of SDC in the decellularization protocol set forth in the Examples and subjecting the resulting sample to histological or immunological examination, or both, to determine whether substantially all epidermal cells of the nipple have been removed. If it has, the bile salt is suitable for use in the protocol.

The sample is then again washed with water for a few hours, preferably about two, and then washed with a saline solution for a few hours, preferably about two, where "about" means plus or minus 15 minutes. The samples are then incubated overnight with 5× streptomycin-penicillin-amphotericin B (sold by a number of suppliers at 100×, including Sigma Aldrich, Lonza Walkerville, Inc. (Walkerville, Md.), the American Type Culture Collection ("ATCC", Manassas, Va.), and EMD Millipore (Billerica, Mass.)), water washed, treated with deoxyribonuclease I ("DNase I") for several hours, preferably about two hours, and then stored in a phosphate buffered saline solution containing 5× streptomycin-penicillin-amphotericin B at 4° C. until use. Using an orbital shaker as an exemplar, the rotations per minute, or rpm, is set to between about 250 and about 400, more preferably about 275 to about 375, still more preferably about 300 to about 350 and most preferably about 325, with "about" in this case meaning 5 rpm on either side of the stated number. Orbital shakers are preferred for their smooth continuous motion and uniform mixing. A number of other shakers are known in the art, including rocking, rolling, reciprocal, overhead, vibrating platform, and rotating shakers. Additionally, other devices, such as rotators, that allow uniform mixing contents of containers over time are known. In general, any shaker, rotator or similar device that provides mechanical agitation of a sample can be used so long as it provides uniform mixing without being so violent that the mixing action disrupts the physical integrity of the sample, such as a nipple or NAC, being decellularized. Depending on the type of shaker or rotator, the speed of the agitation of containers holding the sample may be stated in units other than rpms. It is anticipated that the person of skill will be readily able to determine the appropriate speed setting for the particular shaker or rotator used by reference to the rpm setting for an orbital shaker, as set forth above.

It is believed that the use of NAC in which both the epidermis and the dermis have been decellularized provides a better scaffold for reseeding and formation of an aesthetically satisfying nipple and areola graft.

Production and Use of Decellularized Epidermis

As noted in the preceding section, the methods developed for decellularizing nipples succeeded in decellularizing the nipple epidermis. Since the epidermis covering the nipple is the same or similar to the epidermis of the skin, the protocols used to decellularize both the nipple epidermis and dermis can likewise be used to decellularize skin epidermis, dermis, or both. Epidermis can be separated from the dermis and then decellularized using the protocols disclosed herein, or both the epidermis and the dermis can be decellularized together to provide an acellular matrix that provides both layers.

Skin can be wounded in a variety of ways, including being burned by fire or chemicals or being torn, or torn off, by trauma. According to the product literature for Glyaderm®, a current commercially available acellular dermis, it can be used as a dermal replacement layer under an autologous split thickness skin graft. In some embodiments, the decellularized epidermis provided by the techniques disclosed herein can be used to cover an acellular dermal matrix such as Glyaderm®, thereby reducing the need to provide take epidermis from elsewhere on the patient to cover the acellular dermal matrix. In some embodiments, both the epidermis and the dermis of the donor skin are decellularized so that they can be used to cover a skin wound without needing a separate acellular dermis.

The decellularized epidermis or decellularized epidermis and dermis can be repopulated with cells as described in the section above pertaining to the NAC. As was described with respect to the NAC, in some embodiments, cells to repopulate the decellularized epidermis or epidermis and dermis can be obtained by taking a skin punch from the patient, dissociating the cells of the skin punch, and either incubating the cells with the decellularized material or first expanding the dissociated cells in culture before incubating them with the decellularized material to repopulate it.

A skin wound can be covered by the decellularized epidermis to provide protection. If the skin wound is of a full skin thickness, the wound is preferably overlaid by a decellularized epidermis and decellularized dermis, preferably positioned so that the decellularized dermis faces the interior and the decellularized epidermis faces the exterior. In embodiments in which the decellularized epidermis has not been fully repopulated, once positioned on the skin wound to the practitioner's satisfaction, the decellularized epidermis, dermis, or both is sutured and preferably coated with a biocompatible occlusive coating, as described above. Without wishing to be bound by theory, it is believed that the occlusive coating creates an environment that promotes migration of keratinocytes from the surrounding, uninjured skin, into the decellularized epidermis.

EXAMPLES

Example 1

This example sets forth materials and methods used in studies reported herein.

Decellularization

The process depicted in FIG. 1 used tissue samples collected by trained veterinary technicians at Tulane National Primate Research Center (TNPRC). The technicians collected Rhesus macaque (*Macaca mulatta*) nipple and areola tissue from animals undergoing routine euthanasia due to chronic diarrhea or self-mutilation, as well as from control animals from various experiments. All animal procedures conformed to the requirements of the Animal Welfare Act and all animal protocols were approved by the Institutional Animal Care and Use Committee (IACUC) of the TNPRC before implementation of experimental protocols. Rhesus macaque tissue samples were decellularized through a modified protocol previously described by Bonvillain et. al., Tissue Eng: Part A, 18(23-24): 2437-52 (2012) ("Bonvillain 2012"), and Scarritt et. al., Tissue Eng: Part A, 20(9-10):1426-43 (2014) ("Scarritt 2014"). In brief, after NAC samples were collected, they were exposed to a detergent wash of 0.01% Triton X100 for 4 days, water washed for two hours, followed by another detergent wash of 4% sodium deoxycholate ("SDC") for 4 days, and water washed for 2 hours. After the detergent washing steps were complete, the samples were washed in 992.47 millimolar sodium chloride solution for 2 hours, followed by a 2 hour water wash. Samples were then incubated overnight, at 4° C., in a 1% phosphate buffered saline ("PBS") solution containing 5× penicillin-streptomycin-amphotericin B. After overnight incubation, samples were water washed for 2 hours, treated with DNase I for 2 hours, washed with water for 2 hours and then stored in a 1% PBS solution containing 5× penicillin-streptomycin-amphotericin B at 4° C. until use. Unless otherwise stated, all steps prior to storage were carried out at room temperature and performed on an orbital shaker set to an agitation speed of 325 rpm.

Genomic DNA Isolation, Quantification, and Fragment Analysis

Samples were frozen at −80° C. and then lyophilized for 48 hours using a ModulyoD FreezeDryer (Thermo Electron Corporation, Madison, Wis.) set to −40° C. and a pressure of 80 mm Hg. Using sterile tools, three random portions of the lyophilized samples were dissected, shredded with forceps, and weighed. The samples were then processed in triplicate using a Qiagen DNeasy kit (Valencia, Calif.) according to the manufacturer's instructions. All samples were processed in parallel and the concentration of genomic DNA (gDNA) was quantified using a NanoDrop™ spectrophotometer (Thermo-Fisher Scientific, Waltham, Mass.). gDNA recovered from all samples was precipitated by addition of sodium acetate (final concentration of 0.3M) and 0.7 volumes of 2-propanol. Samples were centrifuged at 15,000×g, at 4° C., for 22 minutes. The resulting pellet was washed with 70% ethanol, centrifuged again for 10 minutes, decanted, and air dried for no more than 15 minutes. The pellet was then resuspended to 1.0 µg/µL in DNA elution buffer provided in the Qiagen DNeasy kit. gDNA fragment sizes were evaluated by gel electrophoresis. gDNA was run on a 1.0% Ultrapure agarose gel (Invitrogen, Life Technologies Corp., Grand Island, N.Y.) with 0.07% ethidium bromide (Promega Corporation, Madison, Wis.). Lastly, 1.5 µg of DNA from each sample was loaded and electrophoresed at 100 volts for 1 hour and 15 minutes. An ImageQuant LAS 4000 (GE Healthcare Life Sciences, Pittsburgh, Pa.) was used to image the gels.

Histological Analysis

Tissue embedding, sectioning, and staining were completed through the Histology Core at the Center for Stem Cell and Regenerative Medicine at Tulane University School of Medicine. Hematoxylin and eosin (H&E) staining for nuclei, Gomori trichrome staining for collagen, and Movat's Modified Pentachrome staining for elastin were accomplished using standard procedures. Briefly, samples were fixed by submersion in 10% neutral buffered formalin (NBF) for at least 24 hours. Next, tissue was paraffin embedded and sectioned to 5 microns in thickness. Paraffin-embedded tissue sections were deparaffinized at 56° C. on a heating block for 30 minutes. Sections were then rehydrated via serial dilutions of ethanol, boiled in sodium citrate buffer (10 mM tri-sodium citrate dehydrate, 0.05% Tween-20, pH 6) for 10 minutes, stained, dehydrated, and mounted with mounting solution before being coverslipped.

Alcian Blue staining for glycosaminoglycans was conducted using Alcian Blue GX8 (Acros Organics, cat: AC400460250, Fisher Scientific Co., LLC, Pittsburgh, Pa.) and countered stained with Safranin O staining. The protocol used was a modified version of the established Abcam protocol (ab150662 Alcian Blue Mucin Stain, Abcam, Cambridge, Mass.).

For immunohistochemical analyses, primary antibodies for laminin (Chemicon cat: 88918), fibronectin (University of Iowa Developmental Studies Hybridoma Bank, Iowa City, Iowa, P1h11), collagen I (cat: MAB3391, EMD Millipore, Billerica, Mass.), collagen VI (EMD Millipore, cat: MAB1944) were raised in mouse. A horseradish peroxidase conjugated goat anti-mouse secondary antibody (Santa Cruz Biotechnology. Inc., Dallas, Tex., cat: SC-2005) was used with all IHC evaluations. All primary antibodies were used at a dilution of 1:200 and secondary antibody was used at dilution of 1:400. An IgG1 control (R&D Systems, Inc., Minneapolis, Minn., cat: MAB398) was used to confirm antibody specificity. After deparaffinization and rehydration through ethanol, tissue sections were boiled for 10 minutes in sodium citrate buffer as previously described. Sections were then blocked for 30 minutes with PerkinElmer Blocking Reagent (PerkinElmer, Waltham, Mass., cat: FP1136). Samples were washed three times with Tris-buffered saline (TBS; 50 mM Tris, 150 mM NaCl, pH 7.6), and then incubated overnight at 4° C. with the primary antibody or IgG1 control in a humidified chamber. The following day, samples were washed with TBS and incubated with secondary antibody at room temperature for 1 hour in a humidified chamber. Sections were washed with TBS and then counterstained with Mayer Modified Hemotoxylin (Newcomer Solutions, Madison, Wis., cat no. 1202). IHC was imaged using an Aperio ScanScope (Aperio, Vista, Calif.) at a magnification of 40×. Images were analyzed using the Aperio ImageScope program.

To verify complete cell removal after decellularization, DAPI staining of tissue sections was conducted for visualization of intact nuclei. Paraffin-embedded tissue sections were placed on a heating block for 30 minutes at 56° C., rehydrated in serial ethanol solutions, and mounted using ProLong™ Gold Antifade reagent with DAPI (Invitrogen). DAPI staining was imaged using a Leica DMRXA2 deconvolution inverted fluorescent microscope (Leica Microsystems, Buffalo Grove, Ill.) fitted with the Cooke SensiCAM camera/controller (Cooke Corp., Auburn Hills, Mich.) and Slidebook software (Intelligent Imaging Innovations, Denver, Colo.).

Protein and GAG Quantification

Samples were frozen at −80° C. and lyophilized as previously described. Using sterile tools, three random portions of the lyophilized samples were dissected, minced with forceps, and massed to approximately 100 mg per sample. The samples were then digested in 1 mL of 100 mM dipotassium phosphate containing 50 µg of proteinase K at 56° C. for 24 hours in a water bath. The proteinase K was then heat inactivated at 90° C. for 10 minutes on a heating block. Samples were cleared twice by centrifugation at 10,000×g for 10 minutes using a fixed angle rotor. Lysate was then filtered with an ultra-free 30,000 NMWL Centricon (EMD Millipore) by centrifugation in a large swinging bucket centrifuge at 3220×g for 45 minutes to remove cellular debris and DNA. Protein concentrations were determined using a Pierce BCA assay (Thermo Fisher Scientific) with bovine serum albumin standards (Pierce). Absorbance was read at 625 nm on a FLUOstar Optima microplate reader. Glycosaminoglycan concentrations were determined by mixing 20 µL of protein lysate with 400 µL of DMMB solution (16 mg/L 1,9-dimethylmethylene blue, 3.04 g/L glycine and 2.37 g/L NaCl, pH 3.0). Absorbance was read at 525 nm using a SmartSpec Plus spectrophotometer (Bio-Rad Laboratories Inc., Hercules, Calif.). Chondroitin sulfate was used to create standard solutions.

Dynamic Cell Seeding

Bone marrow-derived mesenchymal stem cells (BMSCs) from Rhesus macaques isolated by the Tulane Center for Stem Cell Research and Regenerative Medicine Stem Cell Core were used to seed decellularized NAC scaffolds. Cells were plated at 150 cells per $cm^2$ onto a 15 $cm^2$ tissue-culture treated dish. Acellular scaffolds were preconditioned with cell growth media in a cell culture incubator at 5% $CO_2$ and 95% $O_2$ for approximately 30 minutes prior to seeding. Three to five preconditioned acellular scaffolds of dimensions 7 mm×7 mm×2 mm were then placed into a nontreated sterile 10 $cm^2$ plate. Completed conditioned media (α-modified Eagle's medium containing 16.4% fetal bovine serum, 4 mM L-glutamine, 100 U/mL penicillin, 100 µ/mL streptomycin, and 250 ng/mL amphotericin B) was placed into the plates until scaffolds were submerged. Approximately 1 million BMSCs were added per plate. Plates were placed on an orbital rotating shaker in a tissue culture incubator and agitated at a continuous low speed. Seeded scaffolds were removed for analysis at 1, 2, and 7 days. Dynamically seeded scaffolds were assessed via H&E staining and immunohistochemical staining for proliferation, Ki67, and apoptosis, TUNNEL. Ki67 and TUNEL protocol was performed as previously described (Bonvillain, R. W., et al 2012).

Tissue Adhesive Coating

Figure 9:
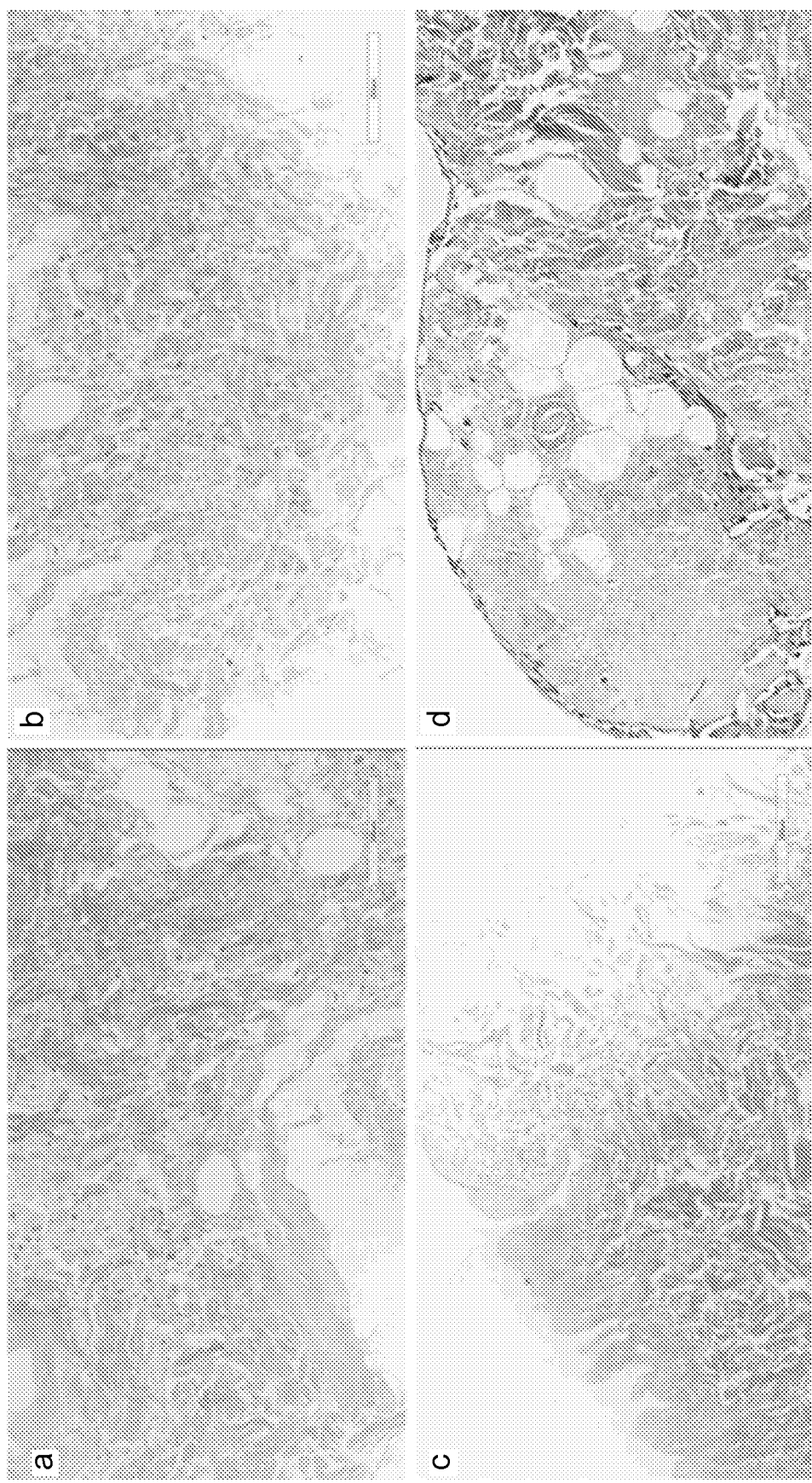
FIG. 9 shows the seeding of keratinocytes on decellularized NAC, in vitro, using H&E staining. a & b) Decellularized NAC scaffold coated with high viscosity tissue adhesive, injection seeded with keratinocytes, 5 days incubation; c) decellularized NAC scaffold not coated with high viscosity tissue adhesive, injected seeded with keratinocytes, 5 days incubation; d) decellularized NAC scaffold not coated with high viscosity tissue adhesive, dynamically seeded with keratinocytes for 7 days. Size bar=200 µm, all images are at 10×. The extracellular matrix shows as light gray, while cells or cell matter and nuclei show as darker gray or dark gray dot.

After grafting the scaffold to the patient, the scaffold and surrounding dermal tissue were coated with Sure+Close II high viscosity tissue adhesive and then injected with neonatal foreskin keratinocytes (passage 6) in several locations throughout the tissue. Samples were grown under normal static cell culture conditions for 5 days. Samples were embedded and sectioned at 5 um, per standard procedures of the Histology Core, located in the Center of Stem Cell Research and Regenerative Medicine, Tulane University Health Science Center, New Orleans La. Coated acellular NAC vs not coated acellular NAC are depicted in FIGS. 9a & b, and FIG. 9c, respectively. FIG. 9d shows acellular NAC scaffold seeded with the same cell line under similar cell culture condition but in dynamic seeding, where the scaffolds were placed in a cell culture dish and cells were introduced into the media surrounding the tissue. The scaffold was then dynamically shaken on an orbital shaker at ~30 rpm overnight and allow to grow for 7 days. In FIGS. 9a & b it is visible that the keratinocytes are not isolated to the edges of the tissue and visually appear to have a higher number of cells as compared to FIGS. 9c & d.

Example 2

This Example sets forth the results of studies conducted in the course of the work reported herein.

Detergent-Based Decellularization Effectively Removes Cells from NAC Tissue

To determine the efficiency of decellularization to remove DNA from rhesus macaque NAC, gDNA was isolated from native and decellularized NAC tissue (FIG. 7A). There was a significant reduction in DNA content with native NAC containing 2,022.71 (SEM: 751.90) ng DNA per mg lyophilized tissue and decellularized NAC containing 56.51 (SEM: 8.45) ng of DNA per mg of lyophilized tissue ($p<0.05$). Gel electrophoresis of 1.5 ug of gDNA from native NAC appeared as a heavy, high molecular weight band, whereas DNA from decellularized NAC consisted of small fragments of degraded DNA that did not create a banding pattern (FIG. 7 B).

Figure 5:
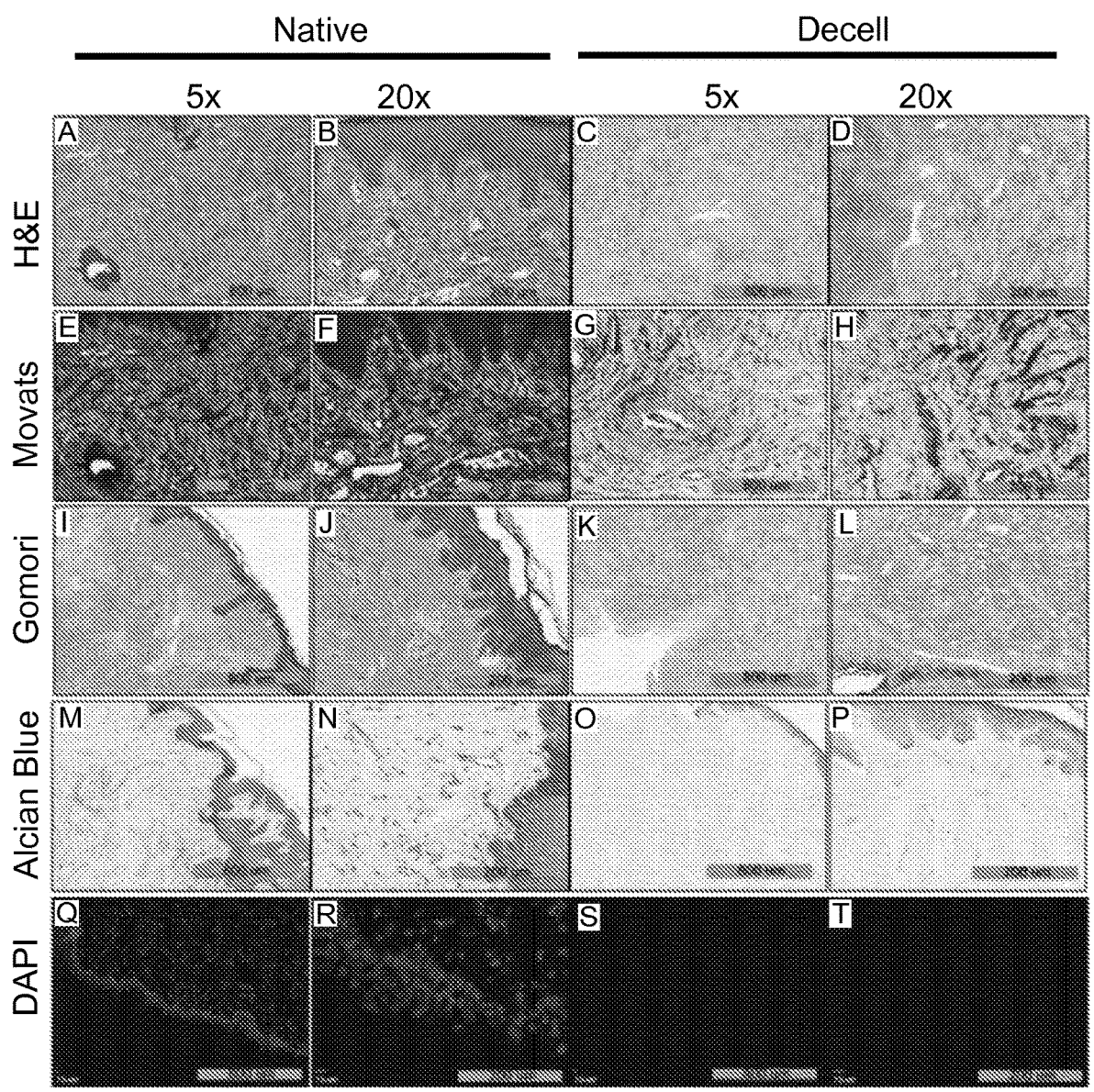
FIG. 5 shows a histological stain and DAPI label of native vs. decellularized NAC. Each row represents a different nuclei or extracellular matrix component stain. The first two columns depicts the native tissue structures and the last two columns depict the decellularized matrix: H&E staining (A-D) with extracellular matrix shown in lighter shades of grey and nuclear material and acidic structures show in dense black; Movat staining (E-F) with Nuclei and elastic fibers shown in dark, dense black; Gomori staining (I-J) with collagen and reticular fibers shown in light grey, dense collagen shown in darker grey, and nuclei show in dark, dense small circles; Alcian Blue staining (M-P) with glycosaminoglycans shown in lighter grey, and nuclei in dense black circles; and DAPI labeling (Q-T) with nuclear material shown in lighter grey circles.
Figure 6:
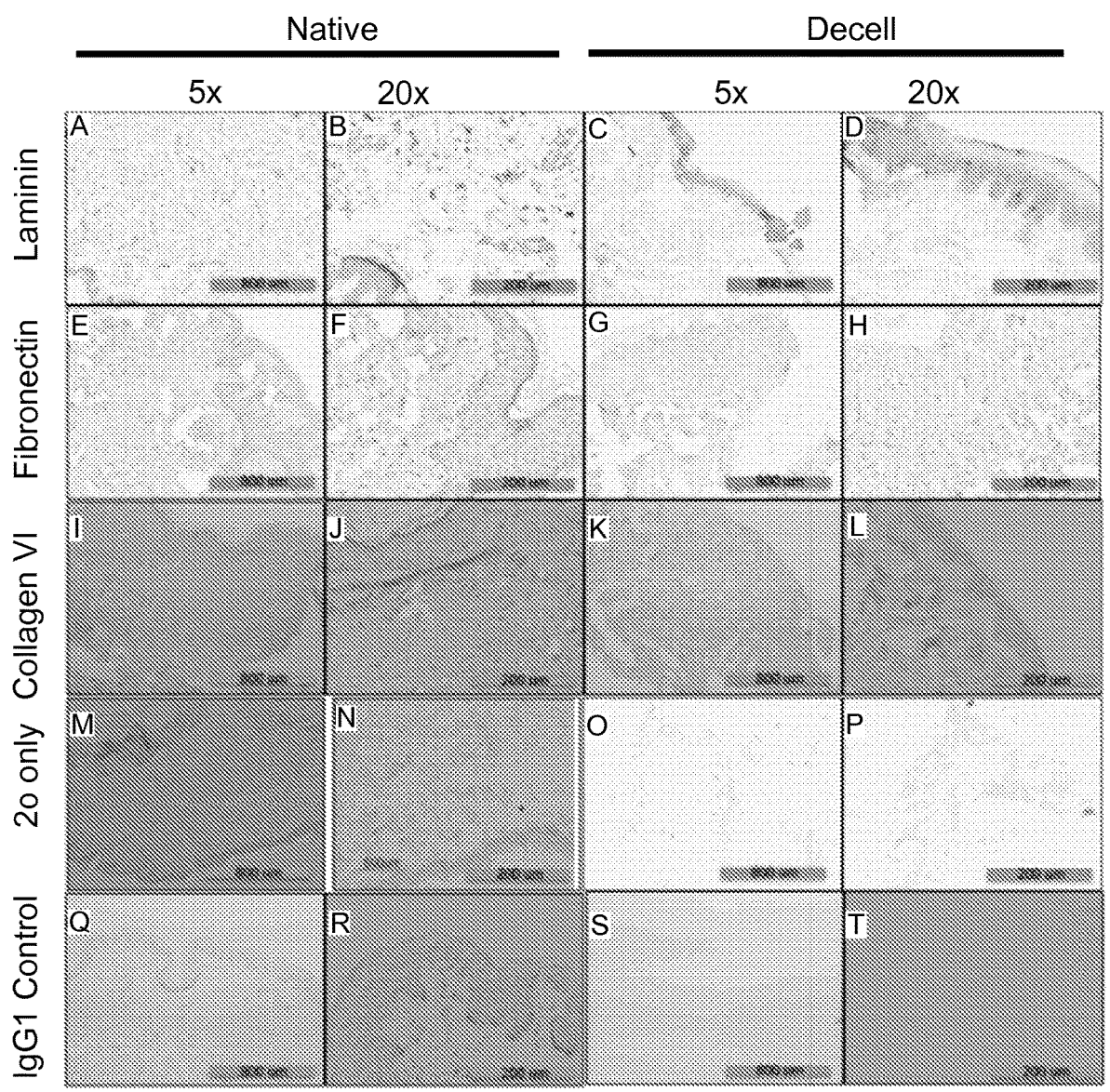
FIG. 6 shows an immunohistochemistry stain of native vs. decellularized NAC. Each row represents a different nuclei or extracellular matrix component stain. The first two columns depict the native tissue structures and the last two columns depict the decellularized matrix. The secondary antibody with a HRP attached was developed with DAB, which developed the antigen of interest a brown color (as depicted in FIG. 6 as grey-to-black shaded areas). The counterstain of the nuclei is shown as purple staining (depicted in FIG. 6 as small dark filled circles.)

To investigate the potential application of decellularization for the generation of tissue-engineering scaffolds for breast reconstruction, NAC tissue was exposed to a series of detergents, salts, and enzymes to lyse cells and remove debris, as detailed in the Materials and Methods section. H&E staining of native NAC tissue showed dense eosin staining in the keratinocyte layer of the epidermis (FIGS. 5A and B). Decellularized macaque NAC tissue showed a lack of hematoxylin-stained nuclei indicating efficient cell removal (FIGS. 5C and D). Complete cell removal was also observed within areas of dense cartilage (FIGS. 5C and D) Immunohistochemistry (IHC) was to visualize distinct proteins in the decellularized matrix and native tissues. It was found that laminin, Fibronectin and Collagen VI were all present in the native as well as the decellularized matrix. FIG. 6. It was visually confirmed using histological techniques that the resulting acellular matrix maintained its structure; overall shape; extracellular component, such as collagen (H&E, Gomori), elastin (Movat's) and glycosaminoglycans (alcian blue); and was lacking visible nuclear material in all histological staining and when specifically staining only for nuclei, via DAPI (FIG. 5).

Protein and GAG Quantification

Glycosaminoglycans (GAG) as a ratio to total protein concentrations were determined to be 0.025 (SEM: 0.004) for the native tissue and 0.068 (SEM: 0.027) for the decellularized tissue (FIG. 7C).

Cell Seeding

The cell seeding of the decellularized NAC scaffold at 1, 2, 3 and 7 days showed that the cells were able to survive after the initial cell seeding until the 7-day time point.

Example 3

This Example discusses the results set forth in the preceding Example.

This study demonstrated that a dermal/semi-glandular structure such as the nipple and areola complex can be sufficiently decellularized. Decellularization efficiency was determined based on three key criteria, as outlined by Crapo et al., Biomaterials, 32(12):3233-43 (2011): no visible signs of cells or cell debris, reduction of DNA to less than 50 ng per mg tissue, and degradation of any remaining DNA to less than 200 bp. These criteria are based on the principle that cellular debris, high concentrations of DNA, or the presence of long DNA fragments in a decellularized tissue are potentially immunogenic and, therefore, detrimental to successful incorporation post-transplantation. The concentration of genomic DNA isolated from decellularized NAC was about 56 ng per mg of lyophilized tissue and no visible banding of DNA fragments were found when DNA from decellularized NAC was electrophoresed. The average 280 nm/260 nm of the DNA was slightly higher than the 1.8 ratio threshold indicating that there may have been protein contamination and that the value of DNA may have been higher as a result. Lyophilization of the NAC tissue removed all of the water, allowing for the reported weight to represent almost all material, potentially leading to slightly higher experimental results. This could lend to the 56 ng of DNA/mg of dried tissue which is just slightly above the threshold described by Crapo et al (2011), supra. Whether or not this small increase in DNA will prove to be significantly immunogenic is yet to be determined.

An advantage to using decellularized whole matrix to reconstruct the NAC, is that the acellular whole NAC maintains both the micro and macro structures of the native tissue, allowing for a regenerative complex that is seemingly aesthetically identical or similar to that of the patients' removed complexes. Therefore, it is important to verify that the extracellular components, collagen, elastin, cell adhesion molecules of the acellular complex, are being maintained during the decellularization process. In this study we looked at the individual ECM components to confirm that the complex structures are intact.

To determine the presence and localization of cell adhesion molecules, fibronectin and laminin; and Collagen VI, immunohistochemistry was used for visual analysis. Both cell adhesion molecules tested, fibronectin and laminin, were found to be present in the decellularized tissue in comparison the native sections tested. The laminin was found to be present throughout the matrix of both the native and decellularized samples; however, it was heavily localized in acellular epidermis, where the dense layer of keratinocytes is localized. The opposite heavy localization expression of fibronectin was shown, where it was ubiquitously seen throughout the acellular and native samples, but heavily localized in the dermis layers. Walter et al., Burns, 24(2):104-13 (2012), showed similar findings with localization of fibronectin; and preservation of fibronectin and laminin after decellularization in a porcine dermis model was also previously verified (Hoganson et. al., Biomaterials, 31(27):6934-40 (2010)). Collagen I and Collagen VI, which are both essential for skin integrity and function, were also shown to be present in the native, as expected, and maintained their residence in the decellularized matrix. Both secondary only and IgG1 controls confirmed that there was only nominal background staining and that non-specific staining of the primary and secondary antibodies were not present.

Histological analysis through H&E showed that the overall structures of the NAC on the micro scale are maintained; the extracellular matrix fibers were intact and no nuclei were found. An overall collagen stain with Gomori showed that collagen, a major extracellular matrix component for the skin, was preserved, however, the decellularized samples did show a slight decrease in color density. Movat's pentachrome staining details elastin fibers—an essential component for skin elasticity. The decrease in overall color density in the Movat's staining is indicative of the removal of the cellular components; however, there are still black fibers present in the acellular matrix, representing that the elastin fibers are preserved during the decellularization process. Alcian Blue was used to verify that the presence of GAGs in the acellular tissue. GAGs are an important component for lubrication of the ECM, especially of skin, since skin is constantly exposed to air. The Alcian blue histological stain confirmed the presence of GAGs in the acellular matrix, with a slight decrease in the blue color density indicating where there may have been a loss of some GAGs during the decellularization process.

Further analysis to elucidate the color density of the Alcian blue through quantification of GAG to protein ratio indicated that there was no significant GAG loss in the decellularized scaffold as compared to native. These findings of decrease in color densities for Gomori staining, Movats stains, GAGs, as well as a similar trend of GAG to total protein concentration, were also found in rhesus macaque lung (Bonvillain 2012, supra), rat lung (Scarritt 2014, supra), and the retention of GAGs in porcine dermis (Hoganson 2010, supra). DAPI labeling as well as counterstains for every immunohistochemical and histochemical analysis, revealed that there were no intact nuclear material visible.

Preliminary cellular seeding of the acellular NAC scaffold, at 1, 2 and 7 day time points indicated that this scaffold allows for a cellular growth permissible microenvironment, where the cells are able to adhere, migrate and proliferate. It was shown that by day 7 there were cells starting to infiltrate deeper into the acellular scaffold.

Figure 8:
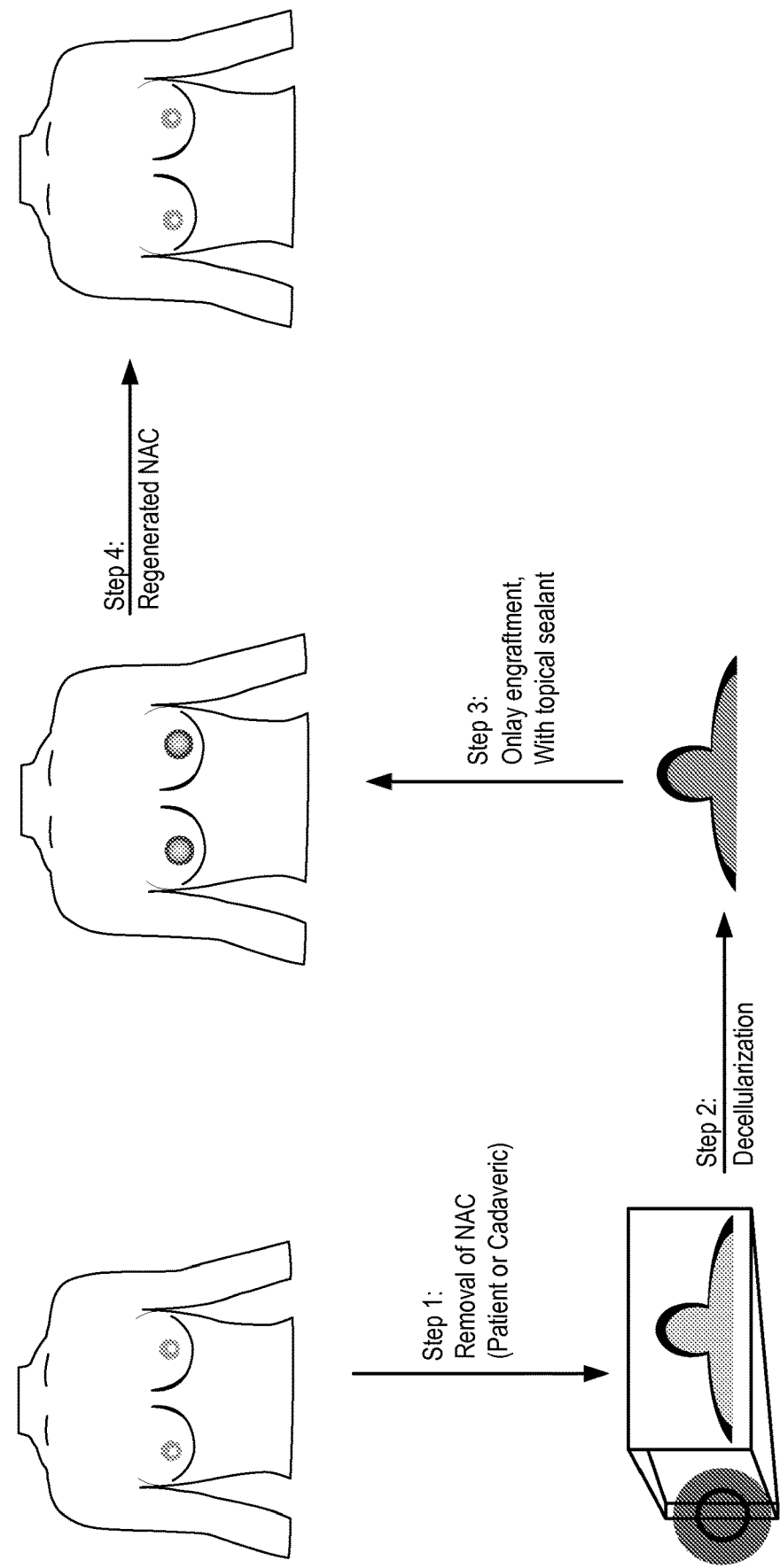
FIG. 8 shows the decellularization and recellularization process of the NAC for human use. In Step 1 the NAC is removed from either the patient, who will then receive their own regenerated NAC, or a cadaveric NAC. In Step 2 the NAC is decellularized by our standard techniques. In Step 3 the acellular NAC graft is engrafted onto patient and a highly viscous topical surgical sealant is applied to act as a foreign body barrier and establish a closed wound coverage. In Step 4 enough time elapses such that cells migrate into the acellular scaffold resulting in a regenerated NAC.

Through preliminary in vitro studies we have shown that by coating decellularized with tissue adhesive, keratinocytes repopulated the acellular NAC scaffold more so visually, as compared to the not-coated, acellular NAC scaffold. This data provides evidence that coating decellularized tissue, such as acellular NAC, with a liquid topical adhesive promotes migration of the patient's cells, such as keratinocytes, into the graft and repopulates the tissue, once the acellular allograft has been engrafted on the patient as described in FIG. 8. We have previously shown (Bonvillain 2012, supra, Bonvillain et al., J Vis Exp (82), e50825, doi:10.3791/50825 2013 ("Bonvillain 2013"), Scarritt 2014, supra) that the micro-structures, including capillaries, and gross structures stay intact after whole organ decellularization. Here we show that the decellularization method can include whole semi-glandular dermal organ NAC structures, and show similar maintenance of ECM and cellular adhesion molecules after decellularization.

Acellular dermal matrix for use in breast reconstruction is already widely used, with an estimated 56% of prosthetic breast reconstructions currently using the commercially available acellular dermal matrices during the procedures. These acellular scaffolds, as previously discussed, are even used to create a structure resembling a NAC, but they do not regenerate or regrow the native NAC tissue. In contrast, the present invention provides a tissue engineering strategy for a complete NAC replacement and reconstruction by using a suitable scaffold for incorporation in total breast reconstruction, exceeding the current standard of nipple protrusion creation through localized skin grafts or creation using simple dermal acellular matrix.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A surgical graft for grafting to a patient, said graft comprising a decellularized nipple, a decellularized areola, or a decellularized nipple attached to a decellularized areola, which decellularized nipple, areola or nipple attached to an areola comprises decellularized epidermis and substantially retains at least one cell adhesion molecule selected from the group consisting of laminin, elastin, fibronectin, and collagen VI.

2. The surgical graft of claim 1, which is a decellularized human nipple.

3. The surgical graft of claim 1, which is a decellularized human areola.

4. The surgical graft of claim 1, which is a decellularized human nipple attached to a decellularized human areola.

5. The surgical graft of claim 1, further wherein said graft substantially retains laminin, fibronectin, and collagen VI.

6. The surgical graft of claim 1, further wherein said graft has been at least partially repopulated by cells after decellularization.

7. The surgical graft of claim 6, wherein said cells are keratinocytes.

8. The surgical graft of claim 7, further wherein said keratinocytes are derived from cells from said patient.

9. A method of making a surgical graft to replace a body part on a patient, said body part having an epidermis and a dermis, and selected from the group consisting of a nipple, an areola, and a nipple attached to an areola, said method comprising:
(a) obtaining a donor nipple, an areola, or a nipple attached to an areola, and,
(b) decellularizing said nipple, areola, or nipple attached to an areola to decellularize cells of the epidermis and cells of the dermis, while substantially retaining at least one cell adhesion molecule selected from the group consisting of laminin, fibronectin, and collagen VI, thereby providing said surgical graft.

10. The method of claim 9, further comprising step (c), incubating said decellularized body part with cells exogenous to said body part under conditions conducive to repopulating said body part with said exogenous cells or cells derived from said exogenous cells.

11. The method of claim 10, further wherein said exogenous cells are keratinocytes derived from said patient.

12. The method of claim 9, wherein said decellularization is by contacting said body part with at least a first detergent and performing a first incubation under conditions sufficient to decellularize said epidermis and said dermis in said body part.

13. The method of claim 12, further wherein said detergent is selected from the group consisting of: 4-(1,1,3,3-Tetramethylbutyl)phenyl-polyethylene glycol, sodium dodecyl sulfate, octylphenoxypolyethoxy-ethanol, 3-[(3-Cholamidopropyl)dimethylammonio]-1-propanesulfonate (CHAPS), and a soluble bile salt.

14. The method of claim 12, wherein said conditions sufficient to decellularize said epidermis and said dermis in said body part include incubating said body part with said at least one detergent at room temperature for at least two days.

15. The method of claim 12, further comprising washing first detergent from said body part following said first incubation and incubating said body part with a second detergent under conditions sufficient to decellularize said epidermis and said dermis in said body part.

16. The method of claim 9, in which said decellularization is of substantially all epidermal cells and substantially all dermal cells in said body part.

17. The method of claim 16, further wherein said body part is a nipple attached to an areola.

18. A method of grafting to a patient in need thereof a body part having an epidermis and a dermis, and selected from the group consisting of a decellularized nipple, a decellularized areola, and a decellularized nipple attached to a decellularized areola, said method comprising:
(a) obtaining a donor nipple, an areola, or a nipple attached to an areola, and
(b) decellularizing said nipple, areola, or nipple attached to an areola to decellularize cells of said epidermis and cells of said dermis while substantially retaining at least one cell adhesion molecule selected from the group consisting of laminin, elastin, fibronectin, and collagen VI,
(c) optionally, repopulating at least some of said decellularized nipple, areola, or nipple attached to an areola with cells exogenous to said body part,
(d) securing said body part to a prepared site on said patient to graft said body part to said patient,
(e) covering said body part with a biocompatible occlusive coating,
thereby grafting said body part to said patient.

19. The method of claim 18, further comprising step (f), allowing time for cells from said patient to integrate into said body part.

20. The method of claim 18, wherein said body part is a decellularized nipple attached to a decellularized areola.

21. The method of claim 18, wherein said cells exogenous to said body part are keratinocytes.

22. The method of claim 21, further wherein said keratinocytes are derived from cells from said patient.

23. The method of claim 18, further wherein said biocompatible occlusive coating is selected from the group consisting of a tissue sealant, a tissue adhesive and a wound sealant.

24. The method of claim 23, wherein said biocompatible occlusive coating is 2-octyl cyanoacrylate.

25. The method of claim 18, further wherein said repopulation in optional step (c) is by incubating the decellularized nipple, areola, or nipple attached to an areola with said exogenous cells ex vivo.

26. A composition comprising substantially decellularized epidermis substantially retaining at least one cell adhesion molecule selected from the group consisting of laminin, elastin, fibronectin, and collagen VI.

27. A composition of claim 26, further comprising substantially decellularized dermis substantially retaining at least one cell adhesion molecule selected from the group consisting of laminin, fibronectin, and collagen VI.

28. A method of providing a protective cover to a skin surface wound, said method comprising step (a), covering said skin surface wound with a composition comprising epidermis in which at least 85% of the cells originally present in said epidermis have been decellularized, and which substantially retains at least one cell adhesion molecule selected from the group consisting of laminin, fibronectin, elastin and collagen.

29. A method of claim 28, further comprising step (b), covering said composition on said skin surface wound with a biocompatible occlusive coating.

30. A method of claim 28, further wherein said substantially decellularized epidermis is at least partially repopulated with cells exogenous to said epidermis prior to step (a).

31. A method of claim 30, wherein said cells exogenous to said epidermis are keratinocytes.

32. The method of claim 31, further wherein said keratinocytes are cells from or derived from cells from said patient.

33. The method of claim 29, further wherein said biocompatible occlusive coating is selected from the group consisting of a tissue sealant, a tissue adhesive and a wound sealant.

34. The method of claim 33, wherein said biocompatible occlusive coating is 2-octyl cyanoacrylate.

35. A method of substantially decellularizing epidermis, said method comprising contacting said epidermis with at least a first detergent and performing a first incubation under conditions sufficient to substantially decellularize said epidermis.

36. The method of claim 35, wherein said detergent is selected from the group consisting of: 4-(1,1,3,3-Tetramethylbutyl)phenyl-polyethylene glycol, sodium dodecyl sulfate, octylphenoxypolyethoxy-ethanol, 3-[(3-Cholamidopropyl)dimethylammonio]-1-propanesulfonate (CHAPS), and a soluble bile salt.

37. The method of claim 35, wherein said conditions sufficient to decellularize epidermal cells in said epidermis include incubating said epidermis with said at least one detergent at room temperature for at least two days.

38. The method of claim 35, further comprising washing first detergent from said epidermis following said first incubation and incubating said epidermis with a second detergent under conditions sufficient to decellularize additional cells of said epidermis.

39. The surgical graft of claim 1, wherein at least 85% of the cells in said epidermis have been decellularized.

40. The surgical graft of claim 1, wherein at least 90% of the cells in said epidermis have been decellularized.

41. The surgical graft of claim 1, wherein at least 95% of the cells in said epidermis have been decellularized.

42. The method of claim 9, wherein at least 85% of the cells in said epidermis have been decellularized.

43. The method of claim 9, wherein at least 90% of the cells in said epidermis have been decellularized.

44. The method of claim 9, wherein at least 95% of the cells in said epidermis have been decellularized.

45. The method of claim 18, wherein at least 85% of the cells in said epidermis have been decellularized.

46. The method of claim 45, wherein at least 90% of the cells in said epidermis have been decellularized.

47. The method of claim 45, wherein at least 95% of the cells in said epidermis have been decellularized.

48. The composition of claim 26, wherein at least 85% of the cells in said epidermis have been decellularized.

49. The composition of claim 48, wherein at least 90% of the cells in said epidermis have been decellularized.

50. The composition of claim 48, wherein at least 95% of the cells in said epidermis have been decellularized.

51. The method of claim 28, wherein at least 90% of the cells in said epidermis have been decellularized.

52. The method of claim 28, wherein at least 95% of the cells in said epidermis have been decellularized.

53. The method of claim 28, further comprising substantially decellularized dermis substantially retaining at least one cell adhesion molecule selected from the group consisting of laminin, fibronectin, and collagen VI.

54. The method of claim 53, wherein at least 85% of the cells in said dermis have been decellularized.

55. The method of claim 53, wherein at least 90% of the cells in said dermis have been decellularized.

56. The method of claim 53, wherein at least 95% of the cells in said dermis have been decellularized.

57. The method of claim 35, wherein at least 85% of the cells in said epidermis are decellularized.

58. The method of claim 57, wherein at least 90% of said cells in said epidermis are decellularized.

59. The method of claim 57, wherein at least 95% of said cells in said epidermis are decellularized.

60. The method of claim 9, wherein said nipple, areola, or nipple attached to an areola, which nipple, areola, or nipple attached to an areola has an extracellular matrix, retains at least 40% of the amount of the cell adhesion molecule present in the extracellular matrix of said nipple, areola, or nipple attached to an areola prior to decellularization.

61. The composition of claim 26, wherein said substantially decellularized epidermis has an extracellular matrix, and said matrix retains at least 40% of the amount of said cell adhesion molecule present in said matrix prior to decellularization.

62. The composition of claim 27, wherein said substantially decellularized dermis has an extracellular matrix, and said extracellular matrix retains at least 40% of the amount of said cell adhesion molecule present in said matrix prior to decellularization.

63. The method of claim 28, further wherein said decellularized epidermis has an extracellular matrix and said extracellular matrix retains at least 40% of the amount of said cell adhesion molecule present in said extracellular matrix of said epidermis prior to decellularization.

64. The method of claim 53, further wherein said decellularized dermis has an extracellular matrix and said extracellular matrix retains at least 40% of the amount of said cell adhesion molecule present in said extracellular matrix of said dermis prior to decellularization.

65. The method of claim 35, further wherein said epidermis has an extracellular matrix having an amount of cell adhesion molecules and wherein said decellularized epidermis retains at least 40% of the amount of a cell adhesion molecule selected from the group consisting of laminin, fibronectin, and collagen present in said extracellular matrix of said dermis prior to decellularization.

66. The surgical graft of claim 1, further comprising substantially decellularized dermis substantially retaining at least one cell adhesion molecule selected from the group consisting of laminin, fibronectin, and collagen.

67. The surgical graft of claim 66, wherein at least 85% of the cells in said dermis have been decellularized.

68. The surgical graft of claim 66, wherein at least 90% of the cells in said dermis have been decellularized.

69. The surgical graft of claim 66, wherein at least 95% of the cells in said dermis have been decellularized.

70. The method of claim 35, further comprising substantially decellularizing dermis attached to said epidermis.

71. The method of claim 70, wherein the at least 85% of the cells in said dermis have been decellularized.

72. The method of claim 70, wherein at least 90% of the cells in said dermis have been decellularized.

73. The method of claim 70, wherein at least 95% of the cells in said dermis have been decellularized.

74. The method of claim 28, wherein said collagen is collagen I.

75. The method of claim 28, wherein said collagen is collagen VI.

* * * * *